(12) United States Patent
Wisman et al.

(10) Patent No.: US 11,813,420 B2
(45) Date of Patent: Nov. 14, 2023

(54) BALLOON CATHETER

(71) Applicant: Medtronic Vascular, Inc., Santa Rosa, CA (US)

(72) Inventors: Elise L. Wisman, Santa Rosa, CA (US); Radhika Bhargav, Mountain View, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 121 days.

(21) Appl. No.: 17/188,321

(22) Filed: Mar. 1, 2021

(65) Prior Publication Data

US 2021/0299417 A1 Sep. 30, 2021

Related U.S. Application Data

(60) Provisional application No. 62/994,567, filed on Mar. 25, 2020.

(51) Int. Cl.
| | |
|---|---|
| *A61M 25/10* | (2013.01) |
| *A61M 25/00* | (2006.01) |
| *A61M 25/01* | (2006.01) |
| *A61M 25/09* | (2006.01) |

(52) U.S. Cl.
CPC .... *A61M 25/1011* (2013.01); *A61M 25/0053* (2013.01); *A61M 25/09* (2013.01); *A61M 25/0108* (2013.01); *A61M 2025/1013* (2013.01)

(58) Field of Classification Search
CPC .......... A61M 25/1011; A61M 25/0053; A61M 25/007; A61M 2025/09125; A61M 2025/1061; A61B 2017/22055; A61B 2017/22068; A61B 2017/22069
See application file for complete search history.

(56) References Cited

U.S. PATENT DOCUMENTS

| | | |
|---|---|---|
| 3,942,517 A | 3/1976 | Bowles et al. |
| 4,353,373 A | 10/1982 | Sessions et al. |
| 4,522,211 A | 6/1985 | Bare et al. |
| (Continued) | | |

FOREIGN PATENT DOCUMENTS

| | | |
|---|---|---|
| CN | 209074607 U | 7/2019 |
| EP | 0371486 A1 | 6/1990 |
| (Continued) | | |

OTHER PUBLICATIONS

International Search Report and Written Opinion of International Application No. PCT/US2021/023794, dated Sep. 1, 2021, 17 pp.

*Primary Examiner* — Katherine H Schwiker
*Assistant Examiner* — Adam J. Cermak
(74) *Attorney, Agent, or Firm* — Shumaker & Sieffert, P.A.

(57) ABSTRACT

In some examples, a catheter includes one or more balloons positioned between an inner wall and an outer wall of an elongated body of the catheter. The one or more balloons are configured to expand through one or more inner wall openings defined by the inner wall and into an inner lumen of the catheter, as well as through one or more outer wall openings defined by the outer wall, e.g., to extend radially away from an outer surface of the outer wall of the catheter. In some examples, the one or more balloons are configured to expand radially inward through the one or more inner wall openings and into the inner lumen of the catheter to contact (e.g., directly contact) a guidewire positioned within the inner lumen.

25 Claims, 8 Drawing Sheets

(56) References Cited

U.S. PATENT DOCUMENTS

| | | | |
|---|---|---|---|
| 4,932,959 A * | 6/1990 | Horzewski | A61M 25/01 604/96.01 |
| 5,163,921 A * | 11/1992 | Feiring | A61M 25/0075 604/537 |
| 5,171,221 A | 12/1992 | Samson | |
| 5,181,921 A | 1/1993 | Makita et al. | |
| 5,275,611 A * | 1/1994 | Behl | A61B 17/34 606/198 |
| 5,299,575 A * | 4/1994 | Sandridge | A61M 25/104 604/913 |
| 5,318,532 A * | 6/1994 | Frassica | A61M 25/104 604/97.01 |
| 5,378,238 A * | 1/1995 | Peters | A61M 25/104 604/99.04 |
| 5,454,789 A * | 10/1995 | Burns | A61M 25/104 604/99.04 |
| 5,545,138 A | 8/1996 | Fugoso et al. | |
| 5,618,266 A * | 4/1997 | Liprie | A61M 25/1002 604/21 |
| 5,628,754 A * | 5/1997 | Shevlin | A61F 2/9526 623/1.11 |
| 5,749,852 A | 5/1998 | Schwab et al. | |
| 6,017,323 A * | 1/2000 | Chee | A61M 25/104 604/249 |
| 6,102,903 A * | 8/2000 | Tremulis | A61M 25/0068 604/249 |
| 6,110,145 A * | 8/2000 | Macoviak | A61M 25/1011 604/101.01 |
| 6,231,543 B1 * | 5/2001 | Hegde | A61M 25/10 606/192 |
| 6,240,323 B1 | 5/2001 | Calenzo, Sr. et al. | |
| 6,251,084 B1 * | 6/2001 | Coelho | A61M 25/09 600/585 |
| 6,277,136 B1 * | 8/2001 | Bonutti | A61B 17/0218 606/190 |
| 6,299,628 B1 * | 10/2001 | Harrison | A61M 25/0105 606/194 |
| 6,786,886 B2 * | 9/2004 | Miller | A61M 25/10 604/96.01 |
| 6,874,621 B2 | 4/2005 | Solosko et al. | |
| 7,479,149 B2 * | 1/2009 | Pallazza | A61M 25/1002 604/509 |
| 8,021,330 B2 * | 9/2011 | McAndrew | A61M 25/10 604/98.01 |
| 8,357,138 B2 * | 1/2013 | Pierpont | A61M 25/1011 604/509 |
| 8,608,688 B2 | 12/2013 | Jain | |
| 8,821,478 B2 * | 9/2014 | Hanson | A61M 25/0043 604/525 |
| 8,926,560 B2 | 1/2015 | Dinh et al. | |
| 9,162,045 B2 | 10/2015 | Jones | |
| 9,402,979 B2 | 8/2016 | Alokaili et al. | |
| 9,717,615 B2 | 8/2017 | Grandt | |
| 9,770,575 B2 | 9/2017 | Wesselmann et al. | |
| 9,907,615 B2 | 3/2018 | Keeler | |
| 9,937,325 B2 | 4/2018 | Shaltis | |
| 10,118,025 B2 * | 11/2018 | Doi | A61M 25/104 |
| 10,188,280 B1 * | 1/2019 | Wall, Jr. | A61M 1/892 |
| 10,994,109 B2 * | 5/2021 | Hakim | A61M 39/10 |
| 11,389,173 B2 * | 7/2022 | Kaufman | A61B 17/1214 |
| 2003/0028234 A1 | 2/2003 | Miller et al. | |
| 2004/0102719 A1 | 5/2004 | Keith et al. | |
| 2005/0131343 A1 | 6/2005 | Abrams et al. | |
| 2007/0118079 A1 * | 5/2007 | Moberg | A61M 25/0097 604/510 |
| 2007/0255380 A1 | 11/2007 | Meyer et al. | |
| 2007/0293719 A1 * | 12/2007 | Scopton | A61B 1/00098 600/106 |
| 2014/0039398 A1 * | 2/2014 | Rottenberg | A61M 25/0606 604/164.01 |
| 2014/0171914 A1 * | 6/2014 | Rowe | A61M 25/02 604/528 |
| 2015/0202415 A1 * | 7/2015 | Fargahi | A61M 25/104 606/194 |
| 2015/0216691 A1 * | 8/2015 | Chuter | A61F 2/82 623/1.11 |
| 2015/0306358 A1 | 10/2015 | Duffy et al. | |
| 2016/0279388 A1 | 9/2016 | Barrish et al. | |
| 2017/0197063 A1 * | 7/2017 | Ahmed | A61M 25/09 |
| 2018/0042691 A1 | 2/2018 | Van Helfteren et al. | |
| 2018/0078743 A1 | 3/2018 | Kubo et al. | |
| 2018/0093073 A1 | 4/2018 | Shimizu et al. | |
| 2019/0167287 A1 | 6/2019 | Vale et al. | |
| 2019/0232045 A1 | 8/2019 | Kaib et al. | |
| 2019/0232071 A1 | 8/2019 | Hulings et al. | |

FOREIGN PATENT DOCUMENTS

| | | |
|---|---|---|
| EP | 0565996 A1 | 10/1993 |
| EP | 0704226 A1 | 4/1996 |
| GB | 2502956 A | 12/2013 |
| JP | 2016198355 A | 12/2016 |
| WO | 2010056879 A1 | 5/2010 |
| WO | 2014/147620 A1 | 9/2014 |
| WO | 2015095416 A1 | 6/2015 |

* cited by examiner

BALLOON CATHETER

This application claims the benefit of U.S. Provisional Patent Application No. 62/994,567, entitled, "BALLOON CATHETER" and filed on Mar. 25, 2020, the entire content of which is incorporated herein by reference.

TECHNICAL FIELD

This disclosure relates to a medical catheter.

BACKGROUND

Medical catheters may be used in various medical procedures. For example, a medical catheter may be used to deliver a medical device or other therapy (e.g., a therapeutic agent) to a target treatment site within a patient. In some cases, a clinician may use a catheter in combination with a guidewire and an outer catheter to reach a target treatment site. For example, the catheter, together with the guidewire, can be used to penetrate and cross a lesion within the vasculature of a patient so that further treatment can be performed, e.g., with a coronary balloon or a stent.

SUMMARY

This disclosure describes example catheters that each include one or more balloons positioned between an inner wall and an outer wall of an elongated body of the catheter. The one or more balloons are configured to expand through one or more inner wall openings defined by the inner wall and into an inner lumen of the catheter, as well as through one or more outer wall openings defined by the outer wall, e.g., to extend radially away from an outer surface of the outer wall of the catheter. In some examples, the one or more balloons are configured to expand radially inward through the one or more inner wall openings and into the inner lumen of the catheter to contact (e.g., directly contact) a guidewire positioned within the inner lumen, which may help provide structural support to the guidewire. For example, the contact between the one or more balloons and the guidewire may help prevent guidewire buckling when the distal end of the guidewire contacts a relatively rigid lesion (e.g., a thrombus, a calcification, a dense fibrous tissue, or the like) within the vasculature of a patient. In some examples, in addition to expanding radially inward, the one or more balloons are configured to expand radially outward through the one or more outer wall openings to help anchor the catheter within the vasculature or other hollow anatomical structure of the patient.

In some examples, the catheter includes a structural support member (e.g., a coil and/or a braid) positioned between the inner and outer walls of the elongated body, and the one or more balloons are configured to expand through at least one gap defined by the structural support member.

In one aspect, the disclosure describes a catheter comprising an elongated body defining a lumen, the elongated body comprising an inner wall defining an inner wall opening and an outer wall defining an outer wall opening. The catheter further comprises a balloon connected to the catheter between the inner wall and the outer wall, wherein the balloon is configured to expand through the inner wall opening into the lumen of the elongated body and through the outer wall opening.

In another aspect, the disclosure describes a catheter comprising an elongated body defining a lumen, the elongated body comprising an inner wall defining a plurality of inner wall openings, an outer wall defining a plurality of outer wall openings, and a structural support member positioned between the inner wall and the outer wall, wherein the structural support member defines a gap. The catheter further comprises a balloon connected to the catheter between the inner wall and the outer wall, wherein the balloon is configured to expand through the plurality of inner wall openings into the lumen of the elongated body and through the plurality of outer wall openings, and through the gap defined by the structural support member.

In another aspect, the disclosure describes a method comprising introducing a catheter into vasculature of a patient, the catheter comprising an elongated body defining a lumen, the elongated body comprising an inner wall defining an inner wall opening and an outer wall defining an outer wall opening. The catheter further comprises a balloon connected to the catheter between the inner wall and the outer wall. The method further comprises inflating the balloon to expand the balloon through the inner wall opening into the lumen and through the outer wall opening.

Clause 1: A catheter comprising: an elongated body defining a lumen, the elongated body comprising an inner wall defining an inner wall opening, and an outer wall defining an outer wall opening; and a balloon connected to the catheter between the inner wall and the outer wall, wherein the balloon is configured to expand through the inner wall opening into the lumen of the elongated body and through the outer wall opening.

Clause 2: The catheter of clause 1, wherein the balloon is configured to expand through the inner wall opening into the lumen to contact a guidewire positioned within the lumen.

Clause 3: The catheter of clause 1 or clause 2, further comprising a structural support member positioned between the inner wall and the outer wall, the structural support member defining a gap, wherein the balloon is configured to expand through the gap.

Clause 4: The catheter of clause 3, wherein the structural support member comprises a coil, and wherein the gap is defined between turns of the coil.

Clause 5: The catheter of clause 4, wherein the coil comprises a proximal coil portion having a first pitch, a distal coil portion having a second pitch, and an intermediate coil portion between the proximal and distal coil portions, the intermediate coil portion having a third pitch greater than at least one of the first pitch or the second pitch.

Clause 6: The catheter of any of clauses 3-5, wherein the structural support member comprises a braid, and wherein the gap is defined by pics of the braid.

Clause 7: The catheter of clause 6, wherein the braid comprises a proximal braid portion having a first braid density, a distal braid portion having a second braid density, and an intermediate braid portion between the proximal and distal braid portions, and, the intermediate braid portion having a third braid density less than at least one of the first braid density or the second braid density.

Clause 8: The catheter of clause 7, wherein the proximal braid portion, the distal braid portion, and the intermediate braid portion have a unibody construction.

Clause 9: The catheter of clause 7 or clause 8, wherein the inner wall opening and the outer wall opening are aligned with the intermediate braid portion along a longitudinal axis of the elongated body.

Clause 10: The catheter of any of clauses 1-9, wherein the inner wall defines a plurality of inner wall openings, the plurality of inner wall openings including the inner wall opening, and wherein and the outer wall defines a plurality of outer wall openings, the plurality of outer wall openings including the outer wall opening, and wherein the balloon is configured to expand through the plurality of inner wall openings into the lumen and through the plurality of outer wall openings.

Clause 11: The catheter of any of clauses 1-10, wherein the catheter comprises a plurality of balloons including the balloon, wherein the inner wall defines a plurality of inner wall openings, the plurality of inner wall openings including the inner wall opening, and wherein and the outer wall defines a plurality of outer wall openings, the plurality of outer wall openings including the outer wall opening, and wherein each balloon of the plurality of balloons is configured to expand through a respective inner wall opening of the plurality of inner wall openings and through a respective outer wall opening of the plurality of outer wall openings.

Clause 12: The catheter of clause 11, wherein the elongated body defines an inflation lumen, and wherein at least two balloons of the plurality of balloons are fluidically coupled to the inflation lumen.

Clause 13: The catheter of clause 11 or clause 12, wherein the elongated body defines a plurality of inflation lumens, and wherein at least two balloons of the plurality of balloons are fluidically coupled to separate inflation lumens of the plurality of inflation lumens.

Clause 14: A system comprising: the catheter of any of clauses 1-14; and a guidewire within the lumen of the elongated body, wherein the balloon is configured to expand through the inner wall opening into the lumen to directly contact the guidewire and secure the guidewire relative to the catheter.

Clause 15: A catheter comprising: an elongated body defining a lumen, the elongated body comprising: an inner wall defining a plurality of inner wall openings; an outer wall defining a plurality of outer wall openings; and a structural support member positioned between the inner wall and the outer wall, wherein the structural support member defines a gap. The catheter further comprises a balloon connected to the catheter between the inner wall and the outer wall, wherein the balloon is configured to expand through the plurality of inner wall openings into the lumen of the elongated body and through the plurality of outer wall openings, and through the gap defined by the structural support member.

Clause 16: The catheter of clause 15, wherein the plurality of inner wall openings and the plurality of outer wall openings are aligned with each other.

Clause 17: The catheter of clause 15 or clause 16, wherein at least one of the plurality of inner wall openings or the plurality of outer wall openings are distributed around an outer perimeter of the inner wall or the outer wall, respectively.

Clause 18: A system comprising: the catheter of any of clauses 15-17; and a guidewire positioned within the lumen of the elongated body, wherein the balloon is configured to expand through the plurality of inner wall openings into the lumen to directly contact the guidewire and secure the guidewire relative to the catheter.

Clause 19: A method comprising: introducing a catheter into vasculature of a patient, the catheter comprising: an elongated body defining a lumen, the elongated body comprising: an inner wall defining an inner wall opening, and an outer wall defining an outer wall opening; and a balloon connected to the catheter between the inner wall and the outer wall. The method further comprises inflating the balloon to expand the balloon through the inner wall opening into the lumen and through the outer wall opening.

Clause 20: The method of clause 19, wherein introducing the catheter into the vasculature comprises introducing the catheter over a guidewire, and wherein inflating the balloon comprises inflating the balloon to expand the balloon through the inner wall opening and into the lumen to directly contact the guidewire and secure the guidewire relative to the catheter.

Clause 21: The method of clause 19 or clause 20, wherein the catheter further comprises a structural support member positioned between the inner wall and the outer wall, the structural support member defining a gap, and wherein inflating the balloon comprises inflating the balloon to expand the balloon through the gap.

Clause 22: The method of clause 21, wherein the structural support member comprises a coil, and wherein the gap is defined between turns of the coil.

Clause 23: The method of clause 21 or clause 22, wherein the structural support member comprises a braid, and wherein the gap is defined by pics of the braid.

Clause 24: The method of any of clauses 19-23, wherein the inner wall defines a plurality of inner wall openings, the plurality of inner wall openings including the inner wall opening, and wherein and the outer wall defines a plurality of outer wall openings, the plurality of outer wall openings including the outer wall opening, and wherein inflating the balloon comprises inflating the balloon to expand the balloon through the plurality of inner wall openings into the lumen and through the plurality of outer wall openings.

Clause 25: The method of any of clauses 19-24, wherein the catheter comprises a plurality of balloons including the balloon, wherein the inner wall defines a plurality of inner wall openings, the plurality of inner wall openings including the inner wall opening, and wherein and the outer wall defines a plurality of outer wall openings, the plurality of outer wall openings including the outer wall opening, wherein inflating the balloon comprises inflating the plurality of balloons to expand each balloon of the plurality of balloons through a respective inner wall opening of the plurality of inner wall openings and through a respective outer wall opening of the plurality of outer wall openings.

Clause 26: The method of clause 25, wherein the elongated body defines an inflation lumen fluidically coupled to at least two balloons of the plurality of balloons, and wherein inflating the plurality of balloons comprises introducing an inflation fluid into the inflation lumen.

Clause 27: The method of clause 25 or clause 26, wherein the elongated body defines a plurality of inflation lumens, wherein at least two balloons of the plurality of balloons are fluidically coupled to separate inflation lumens of the plurality of inflation lumens, and wherein inflating the plurality of balloons comprises separately inflating at least two balloons of the plurality of balloons by at least introducing inflation fluid into the respective inflation lumens.

The details of one or more aspects of the disclosure are set forth in the accompanying drawings and the description below. Other features, objects, and advantages of the systems and techniques described in this disclosure will be apparent from the description and drawings, and from the claims.

BRIEF DESCRIPTION OF THE DRAWINGS

Like reference characters denoted like elements throughout the description and figures.

DETAIL DESCRIPTION

Figure 1:
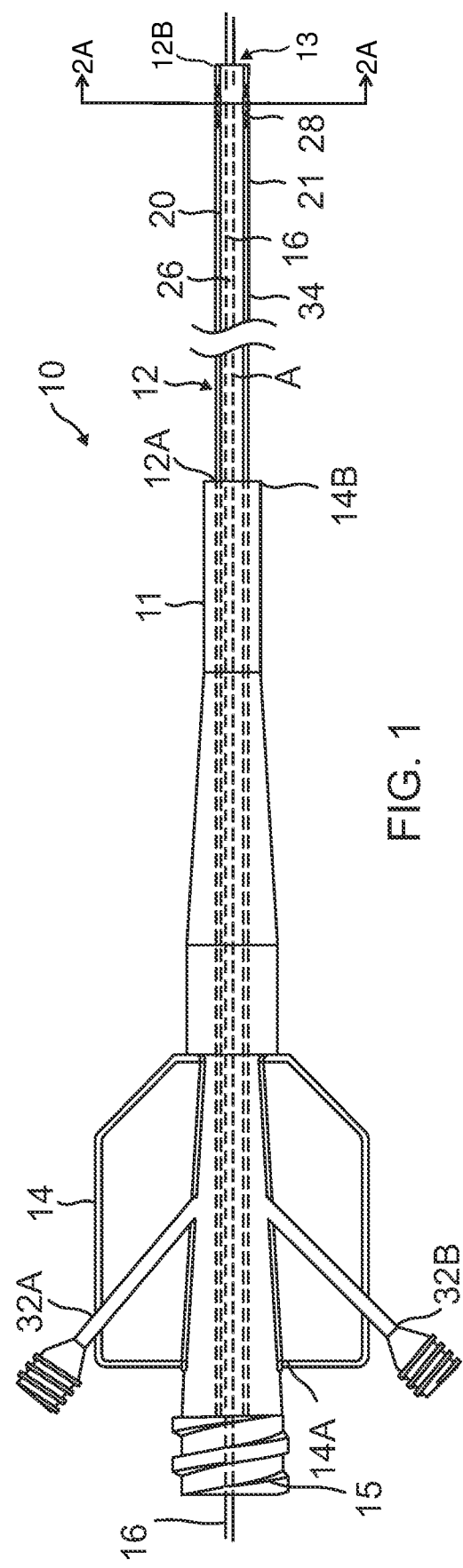
FIG. 1 is a side elevation view of an example catheter, which includes an elongated body, a hub, and one or more balloons.

In examples described herein, a catheter includes an elongated body comprising an inner wall and an outer wall, and one or more balloons connected to the elongated body between the inner wall and the outer wall. For example, the one or more balloons can be attached (e.g., bonded, adhered, or otherwise connected) to the inner wall, the outer wall, or both the inner wall and the outer wall. The inner wall defines at least one inner wall opening open to an inner lumen defined by the elongated body and the outer wall defines at least one outer wall opening open to an environment external to the catheter. In some examples, each inner wall opening may be fully or partially aligned with at least one outer wall opening, e.g., along a longitudinal axis of the elongated body and an axis orthogonal to the longitudinal axis. The alignment along an axis orthogonal to the longitudinal axis can refer to, for example, circumferential alignment in the case of a catheter having a circular cross-section. In other examples, at least one inner wall opening may be longitudinally offset from at least one outer wall opening and/or offset along the axis orthogonal to the longitudinal axis.

The one or more balloons are configured to expand through one or more inner wall openings and into the inner lumen, as well as configured to expand through one or more outer wall openings. For example, when the one or more balloons are in a deflated configuration, the one or more balloons may not extend through some or any of the one or more inner wall openings and/or through some or any of the one or more outer wall openings, and when the one or more balloons are in an expanded configuration, the one or more balloons may extend through the one or more inner wall openings and into the inner lumen, as well as extend through the one or more outer wall openings and radially away from an outer surface of the outer wall.

In the expanded configuration of the one or more balloons, the one or more balloons are configured to engage (e.g., directly contact or contact via an inner liner of the catheter) a guidewire positioned within the inner lumen of the elongated body to help provide structural support to the guidewire. The structural support provided by the one or more balloons may help prevent or reduce guidewire buckling or guidewire jumping when a distal end of the guidewire contacts a relatively rigid material, e.g., a lesion or other occlusion within vasculature of a patient. For ease of description, the relatively rigid material is primarily referred to herein as a lesion; in other examples, however, the relatively rigid material that can cause guidewire buckling or jumping can be any relatively rigid material, such as, but not limited to, other occlusions in a blood vessel of a patient (e.g., a thrombus, dense fibrous tissue, and the like). When a distal end of the guidewire contacts a lesion while a distal pushing force is being applied to the guidewire, the guidewire may deform (e.g., buckle and/or curve away from the lesion), which may interfere with the ability of the guidewire to penetrate (e.g., cross-through within the vasculature) the lesion. In some cases, the distal end of the guidewire may be diverted from its intended path in the vasculature when the distal end contacts the lesion, which may cause the guidewire to jump subintimally into a vessel wall or perforate the vessel wall completely.

In addition, in the expanded configuration of the one or more balloons, the one or more balloons are configured to expand through the one or more outer wall openings to engage with walls of a blood vessel, which can help secure (e.g., fix) the position of the catheter relative to the blood vessel alone or in combination with other balloons of the catheter. Thus, the one or more balloons of example catheters described herein may engage a guidewire within an inner lumen of the catheter and walls of a blood vessel (or other hollow anatomical structure) at the same time to provide support to the guidewire, while anchoring the catheter in the blood vessel. In some examples, in the expanded configuration, the one or more balloons are configured to grip the guidewire to help secure a position of the guidewire relative to the catheter. In other examples, in the expanded configuration, the one or more balloons are configured to enable the guidewire to longitudinally slide relative to the one or more balloons while still providing structural support to the guidewire.

While blood vessels of a patient are primarily referred to herein, in other examples, the catheters described herein may be within other hollow anatomical structures of a patient.

Example catheters described herein include a relatively flexible elongated body (also referred to as a catheter body or an elongated member in some examples) configured to be navigated through vasculature of a patient. The elongated body includes an inner wall and an outer wall, e.g., coaxially arranged and, in some examples, coterminous at the respective proximal ends and/or at the respective distal ends. In some examples, the inner and outer walls are directly connected to each other along at least some length of the catheter. In addition or instead, in some of examples, the inner and outer walls may be separated from each other, e.g., by an intermediate layer, a structural support member (e.g., a braid and/or a coil), or any combination thereof. For example, the innermost surface of the outer wall can be separated from an outermost surface of the inner wall by any suitable distance, such as, but not limited to about 0.05 millimeters (mm) to about 0.5 mm, where the distance is measured in a radial direction in the case of an elongated body having a circular cross-section.

The inner and outer walls may be formed from any suitable material, such as, but not limited to, a polymer, e.g., aliphatic polyamide, thermoplastic elastomer, thermoplastic polyurethane, or combinations thereof. In some examples, the inner and outer walls are formed from the same material. In other examples, the inner and outer walls are formed from different materials. In addition, in some examples, the inner wall and/or outer wall may include only one layer of material, while in other examples, the inner wall and/or the outer wall includes a plurality of layers of material. The plurality of layers of material can be attached to each other (e.g., bonded), or may be separate from each other.

One or more balloons are mechanically connected to the elongated body between the inner wall and the outer wall using any suitable technique, such as, but not limited to, welding, adhesive, attachment mechanisms (e.g., bands on proximal and distal portions of the balloons), or the like or combinations thereof. For example, proximal and distal ends of the balloons may be mechanically connected to an outer surface of the inner wall and/or to an inner surface of the outer wall. The proximal and distal ends of each of the one or more balloons remain connected to the elongated body between the inner wall and the outer wall even when the balloons are inflated. Connecting the one or more balloons between the inner wall and the outer wall of a catheter, rather than, for example, within the inner lumen of the elongated body or an outer surface of elongated body, can help the catheter maintain a relatively low overall outer profile (e.g., diameter or other maximum cross-sectional dimension, the cross-section being taken in a direction orthogonal to a longitudinal axis of the elongated body).

In some examples, the elongated body of the catheter can include one or more layers in addition to the inner wall and the outer wall. For example, the elongated body can include an inner liner that defines an inner lumen of the catheter. As another example, the elongated body can include a structural support member positioned between the inner and outer walls of the elongated body, and at least one balloon positioned between the inner and outer walls is configured to expand through a gap defined by the structural support member. For example, the structural support member may include a coil, and a balloon can be configured to expand through turns of the coil to expand radially inward through an inner wall opening and/or radially outward through an outer wall opening. This enables the structural support member to provide force and/or torque transmission from a proximal side of the balloon to a distal side of the balloon. In contrast, if the coil or other structural support member terminated proximal to the balloon, then started again distal to the balloon, less force and/or torque applied to the catheter on a proximal side of the balloon would be transmitted to a distal side of the balloon.

As another example, the structural support member may include a braid in addition to or instead of a coil, and a balloon can be configured to expand through the pics of the braid to expand radially inward through an inner wall opening and/or radially outward through an outer wall opening. In some examples, the braid includes a proximal braid portion, a distal braid portion, and an intermediate braid portion between the proximal and distal braid portions. The intermediate braid portion has a braid density less than the braid density of the proximal braid portion and/or the braid density of the distal braid portion. At least one inner wall opening and at least one outer wall opening are aligned with the intermediate braid portion, such that the balloon expands through the braid along the intermediate braid portion.

If a structural support member includes both a coil and a braid, then the coil and the braid can have any suitable arrangement relative to each other. For example, the coil and the braid may be longitudinally separated from each other or may partially or fully overlap in a radial direction.

In some examples, a catheter includes a plurality of balloons that are longitudinally aligned. When inflated, the plurality of balloons are configured to expand through a plurality of inner wall openings to provide support to a guidewire positioned within the inner lumen of the elongated body and configured to expand through a plurality of outer wall openings to anchor the catheter in vasculature of a patient. In some examples, each balloon of the plurality of balloons is configured to expand substantially the same distance away from an outer surface and/or inner surface of the elongated body in the respective inflated states. In other examples, at least two balloons of the plurality of balloons are configured to expand different distances away from an outer surface and/or inner surface of the elongated body in the respective inflated states.

In some examples, at least two balloons of the plurality of balloons are fluidically coupled to separate inflation lumens of a plurality of inflation lumens. This may enable a clinician to inflate balloons separately to aid navigation of the catheter to a target treatment site within vasculature of a patient. For example, selective expansion of a subset of the plurality of balloons (e.g., just one balloon or more than one but less than all the balloons) may help modify the position of the catheter in a vessel relative to a center of the vessel, e.g., to re-center the catheter in the vessel or to better position the catheter for navigation around a curvature in the vasculature. As another example, a balloon closer to the catheter distal tip can be beneficial in reducing guidewire buckling and/or jumping when the guidewire starts to penetrate through a relatively rigid vasculature whereas another balloon more proximally can be beneficial as the catheter and guidewire advance through the relatively rigid material.

In addition to or instead of separate inflation lumens, in some examples, at least two balloons of the plurality of balloons are fluidically coupled to a common inflation lumen. Compared to an example in which each balloon is fluidically coupled to a separate inflation lumen, a catheter configuration in which at least two balloons are fluidically coupled to a common inflation lumen may help the catheter maintain a relatively low profile configuration.

The example catheters described herein may be used for any suitable medical procedure, such as, but not limited to, procedures to treat defects in the neurovasculature, peripheral vasculature, and coronary vasculature. Example defects include, but are not limited to, vessel occlusions (e.g., caused by dense fibrous caps), aneurysms, arterial malformations, and the like. For example, to cross or penetrate a lesion within a blood vessel of a patient, a clinician may navigate a guidewire through the vasculature of the patient to a location near the lesion, deliver a catheter to the location over the guidewire, couple the guidewire and the catheter together using the one or more balloons described herein, and penetrate the lesion with the coupled guidewire and catheter.

FIG. 1 is a side elevation view of an example catheter 10, which is configured to provide structural support to a guidewire 16 positioned in an inner lumen 26 of the catheter 10. The catheter 10 can be used with any suitable medical procedure. For example, the catheter 10 can be used in conjunction with the guidewire 16 to penetrate (e.g., partially or fully cross) an occlusion in a blood vessel of a patient.

The catheter 10 includes an elongated body 12 (also referred to herein as a catheter body in some examples) and a balloon 28. The elongated body 12 includes an inner wall 20 and an outer wall 21, and, in some examples, a structural support member 22 (FIGS. 2A-3B) positioned between the inner and outer walls 20, 21. In addition, in some examples, the elongated body 12 can include one or more structures in addition to the inner wall 20, the outer wall 21, and the structural support member 22. For example, the elongated body 12, as well as other elongated bodies described herein, can in some examples include an inner liner radially inward of the inner wall 20, as described with reference to the inner liner 84 shown in FIGS. 5A and 5B. The inner liner can define an inner lumen 26 of the elongated body 12.

The elongated body 12 extends along a central longitudinal axis A from a proximal end 12A to a distal end 12B and defines at least one inner lumen 26 (e.g., one inner lumen, two inner lumens, or three inner lumens), where at least one lumen terminates at a distal opening 13 defined by the elongated body 12. In some examples, the elongated body 12 includes a tubular body. In the example shown in FIG. 1, the proximal end 12A of the elongated body 12 is received within a hub 14 and is mechanically connected to the hub 14 via an adhesive, welding, or another suitable technique or combination of techniques. An opening 15 defined by the hub 14 and located at a proximal end 14A of the hub 14 is aligned with the inner lumen 26 of the elongated body 12, such that the inner lumen 26 may be accessed via the opening 15.

The elongated body 12 may have any suitable dimensions, which may depend upon the medical procedure with which the catheter 10 is intended to be used. For example, the elongated body 12 can have any suitable length, such as, but not limited to, about 50 centimeters (cm) to about 150 cm, such as about 75 cm, about 90 cm, or about 135 cm (e.g., exactly these lengths or approximately these lengths to the extent permitted by manufacturing tolerances), and may be formed from any suitable material. For example, the elongated body 12 may be formed from a metal, a polymer, or combinations thereof.

In some examples, an outer diameter of the elongated body 12 may be about 2 French to about 12 French, such as about 3 French or about 6 French. The measurement term French, abbreviated Fr or F, is three times the diameter of a device as measured in mm. Thus, a 6 French diameter is about 2 mm (e.g., about 1.8 mm), a 5 French diameter is about 1.67 mm, a 4 French diameter is about 1.33 mm, and a 3 French diameter is about 1 mm. The term "about" as used herein with dimensions may refer to the exact value of the such as when used to describe numerical values, "about" or "approximately" refers to a range within the numerical value resulting from manufacturing tolerances and/or within 1%, 5%, or 10% of the numerical value. For example, a length of about 10 mm refers to a length of 10 mm to the extent permitted by manufacturing tolerances, or a length of 10 mm+/−0.1 mm, +/−0.5 mm, or +/−1 mm in various examples.

In some examples, at least a portion of an outer surface 34 of the elongated body 12 includes one or more materials, such as, but not limited to, an anti-thrombogenic coating, which may help reduce the formation of thrombi in vitro, an anti-microbial coating, and/or a lubricating coating. The lubricating coating may be configured to reduce static friction and/kinetic friction between the elongated body 12 and tissue of the patient as the elongated body 12 is advanced through the vasculature. The lubricating coating can be, for example, a hydrophilic coating. In some examples, the entire working length of the elongated body 12 (from the distal portion 14B of the hub 14 (or the strain relief member 11 to the extent it is separate from the hub 14) to the distal end 12B of the elongated body 12) is coated with the hydrophilic coating. In other examples, only a portion of the working length of elongated body 12 coated with the hydrophilic coating. This may provide a length of the elongated body 12 distal to hub 14 with which the clinician may grip the elongated body 12, e.g., to rotate the elongated body 12 or push the elongated body 12 through vasculature or other hollow anatomical structure of a patient.

In some examples, the elongated body 12 may include one or more radiopaque markers, which may help a clinician determine the positioning of the catheter 10 relative to a target treatment site. For example, one or more radiopaque markers may be positioned proximal, within the elongated body 12, adjacent to the balloon 28, or combinations thereof.

The inner wall 20 of the elongated body 12 is radially inward of the outer wall 21 of the elongated body 12, such that the inner wall 20 is closer to the inner lumen 26 than the outer wall 21. In some examples, an inner surface of the inner wall 20 defines the inner lumen 26, although a coating, such as a lubricious coating, may be positioned along the inner surface of the inner wall 20 in some examples. The inner wall 20 and the outer wall 21 have any suitable configuration. For example, the inner wall 20 and the outer wall 21 may be respective layers of a multi-layer elongated body 12, and can each include one layer or a plurality of layers. Although a gap is shown between the inner wall 20 and the outer wall 21 in some of the figures, in some examples, the inner wall 20 and the outer wall 21 may contact each other directly in at least some sections along a length of the elongated body 12, or may be separated from each other by another layer, such as a tie layer or another intermediary layer. For example, the inner and outer walls 20, 21 may be attached to each other directly or indirectly via a tie layer. In other examples, the inner and outer walls 20, 21 are not attached to each other.

The inner and outer walls 20, 21 may be formed from any suitable material, such as, but not limited to the example polymers discussed above with respect to the elongated body 12. In examples in which the inner wall 20 and/or the outer wall 21 include a plurality of layers, the plurality of layers of the respective wall 20, 21 can be formed from the same material or at least two layers of the plurality of layers can be formed from different materials, which can be selected to provide the elongated body 12 with various desirable structural characteristics. In some examples, the inner and outer walls 20, 21 are formed from the same material, while in other examples, the inner and outer walls 20, 21 are formed from different materials. In addition, in some examples, the inner and outer walls 20, 21 may have substantially the same (e.g., the same but for manufacturing tolerances) thicknesses, where a thickness is measured in a direction orthogonal to the central longitudinal axis A. In other examples, the inner and outer walls 20, 21 have different thicknesses. A thickness of each of the walls 20, 21 may depend upon the intended use of the catheter 10. For example, in some examples, a thickness of each of the walls is about 0.02 mm to about 5 mm.

The inner wall 20 defines at least one inner wall opening 30 (shown individually in other figures as inner wall openings 30A-30D) through which the balloon 28 is configured to expand into to enter the inner lumen 26 when the balloon 28 is in its expanded state (also referred to herein as an inflated state). The inner wall openings 30 can be distributed along a perimeter of inner wall (e.g., circumferentially distributed in the case of an inner wall having a circular cross-section) and/or longitudinally distributed along longitudinal axis A. In some cases, for example, inner wall openings 30 are longitudinally aligned, but circumferentially distributed along the inner surface of the inner wall 20. The inner wall openings 30 can be evenly distributed, or unevenly distributed. In addition to or instead of being separated from each other along a perimeter of inner wall (e.g., circumferentially separated), the inner wall openings 30 can be longitudinally separated from each other along longitudinal axis A.

The outer wall 21 defines at least one outer wall opening 31 (shown individually in other figures as outer wall openings 31A-31D) through which the balloon 28 is configured to expand radially outward away from the outer surface 34 of the elongated body 12 when the balloon 28 is in its expanded state. As with the inner wall openings 30, the outer wall openings 31 can be distributed along a perimeter of inner wall (e.g., circumferentially distributed in the case of an outer wall having a circular cross-section) and/or longitudinally distributed along longitudinal axis A.

Although elongated bodies of catheters, inner walls, and outer walls having circular cross-sections are primarily described herein for ease of description, in other examples, elongated bodies of catheters, inner walls, and/or outer walls can have other cross-sectional shapes, the cross-section being taken in a direction orthogonal to the central longitudinal axis of the respective elongated body, the inner wall, or the outer wall.

In the expanded configuration within the vessel 38, the balloon 28 may conform to engage with the walls of the vessel 38 to anchor the elongated body 12 in the vessel and engage with the guidewire 16 to provide structural support to the guidewire 16. The balloon 28 may be formed from any suitable material, such as, but not limited to, crylonitrile-butadiene styrene (ABS), polyamides, for example, nylons, polyamide 6 (PA 6), or polyamide 66 (PA 66), polycarbonates (PC), polyethylenes (for example, high density polyethylenes (HDPE) or low density polyethylenes (LDPE)), poly(methyl methacrylate) (PMMA), polyoxymethylene (POM), polypropylenes (PP), polystyrenes (PS), polybutylene terephthalate (PBT), styrene acrylonitrile resin (SAN), thermoplastic elastomers (TPE) (for example, polyether block amides (PEBAs)), polyphenylene sulfide (PPS), polyetheretherketones (PEEK), polyurethanes, polyesters, or blends, copolymers, or coextrusions thereof. The balloon 28 may be inflated to any suitable pressure via an inflation fluid (e.g., saline) delivered to the balloon 28 via an inflation lumen defined by the elongated body 12 (e.g., between the inner and outer walls 20, 21). In some examples, the balloons 28 may be inflated to a pressure of about 2-6 atmospheres. The balloons 28 may be configured to be deflated via a vacuum or other stable source applied to the one or more inflation lumen to forcibly remove the inflation fluid from the balloon 28.

The balloon 28 may be of any suitable size or shape. In some examples, the balloon 28 may define a cross sectional diameter in the expanded configuration equal to or greater than the cross-sectional diameter of the blood vessel 38 (e.g., on the order of about 2 mm to about 4 mm). Additionally, or alternatively, the balloon 28 may exhibit a cross sectional diameter that is configured to conform to a range of vessel diameters when inflated to the expanded configuration. The balloon 28 can have any suitable length. In some examples, the balloon 28 has a length of about 0.2 cm to 5 cm. In some examples, a distal-most end of the balloon 28 is separated from the distal end 12B of the elongated body 12 by a distance of about 1 cm to about 10 cm, although other balloon positions can be used in other examples.

As discussed with reference to FIGS. 2A and 2B, the balloon 28 is configured to simultaneously expand through the at least one inner wall opening 30 and the at least one outer wall opening 31. In some examples, the outer wall openings 31 may be fully or partially longitudinally and/or circumferentially aligned with at least one inner wall openings 30 (e.g., the spacing and shape of the outer wall openings 31. In other examples, at least one inner wall opening 30 may be longitudinally and/or circumferentially offset from at least one outer wall opening 31. In addition, in some examples, there may be an equal number of inner wall openings 30 and outer wall openings 31. In other examples, however, there may be a greater or fewer number of inner wall openings 30 compared to outer wall openings 31.

The inner wall openings 30 and the outer wall openings 31 have any suitable size, which may depend on one or more factors, such as, but not limited to, the number of openings 30, 31, the size of the balloons, the number of balloons, and the medical procedure for which the catheter 10 is intended to be used. The inner wall and outer wall openings 30, 31 can be circular, elliptical, or any other shape suitable for the balloon 28 to expand through. In some examples, the inner wall openings 30 have an average maximum cross-sectional dimension of 0.01 mm to about 2 mm, and the outer wall openings 31 have an average maximum cross-sectional dimension of 0.01 mm to about 2 mm. The size and/or number of the inner wall openings 30 can depend on the guidewire diameter of the guidewire 16 positioned in the inner lumen 26 of the elongated body 12, e.g., selected to enable the balloon 28 to expand into the inner lumen 26 a sufficient amount to engage the guidewire 16. The size and/or number of the outer wall openings 31 can depend on the size of the blood vessel (e.g., blood vessel diameter to which the catheter 10 is configured to be apposed). For example, the size and/or number of the outer wall openings 31 are selected to enable the balloon 28 to expand into through the outer wall openings 31 a sufficient amount to engage the inner wall of the blood vessel.

The inner wall and outer wall openings 30, 31 may be formed by any suitable technique. In some examples, the openings 30, 31 are formed by a mechanical technique, such as, but not limited to, laser cutting, drilling, punching, or combinations thereof. In other examples, openings 30, 31 are formed by a chemical technique, such as, but not limited to, the selective dissolution of one or more sections of the respective inner and outer walls 20, 21.

As described in further detail with respect to the examples of FIGS. 3A-4B, in some examples, the elongated body 12 includes a structural support member (e.g., a coil and/or a braid) positioned between the inner and outer walls 20, 21, or between an inner liner (not shown in FIGS. 1-4B) and the inner wall 20, the inner wall being positioned radially inward of the inner wall 20 and closer to the inner lumen 26. The structural support member is configured to increase the structural integrity of the elongated body 12 while enabling the elongated body 12 to remain relatively flexible. For example, the structural support member may be configured to help the elongated body 12 substantially maintain its cross-sectional shape or at least help prevent the elongated body 12 from buckling or kinking as it is navigated through tortuous anatomy.

In some examples, the structural support member includes one or more braids each defining a plurality of pics, one or more coils each defining a plurality of turns (e.g., in the shape of a helix), or a combination of one or more braids and one or more coils. For example, a proximal portion of the structural support member may include a braid and a distal portion of the structural support member may include a coil, or vice versa. As another example, a braid and a coil may fully or partially overlap in some examples.

The structural support member may be formed from any suitable material, such as a metal, a polymer, or combinations thereof. In some examples, the structural support member is formed from a shape memory material, such a nickel titanium alloy (Nitinol). In some examples, the structural support member is formed from stainless steel. In some cases, a nickel titanium alloy may be more crush resistant than stainless steel, and, therefore, may be used to form a structural support member of a catheter that is more resistant to kinking and buckling compared to stainless steel.

As discussed in further detail below with reference to FIGS. 3A-4B, the structural support member defines a gap through which the balloon 28 can expand when expanding through the inner wall openings 30 into the inner lumen 26 and/or when expending through the outer wall openings 31 and away from the outer surface 34 of the elongated body 12. For example, in examples in which the structural support member includes a coil, the gap is defined between turns of the coil, and the balloon 28 can be positioned and configured to expand through the turns of the coil to expand into the inner lumen 26 of the catheter 10 and/or expand through turns of the coil to expand radially from the outer surface 34. As another example, in examples in which the structural support member includes a braid, the gap is defined by pics of the braid, and the balloon 28 can be positioned and configured to expand through the pics of the braid to anchor the catheter in the vasculature.

As described in further detail below, the balloon 28 is configured to provide structural support to the guidewire 16 positioned within the inner lumen 26, e.g., to enable the guidewire 16, alone or in combination with the elongated body 12, to penetrate a lesion within a blood vessel of a patient. The guidewire 16 has a relatively flexible configuration to enable a clinician to navigate the guidewire 16 from an access point (e.g., at a femoral artery or a radial artery) through vasculature and to a target treatment site within the patient. Depending on the hardness of the lesion, it may be relatively difficult for the guidewire 16 to penetrate the lesion without additional structural support, e.g., holding it centered within the inner lumen 26 or within the blood vessel. For example when a distal end 16B of the guidewire 16 contacts a relatively rigid material, e.g., a lesion or other occlusion within vasculature of a patient, while a distal pushing force is being applied to a proximal portion of the guidewire 16, e.g., near a proximal-most end of the guidewire 16, a distal portion of the guidewire 16 may buckle or otherwise deform, which may interfere with the ability of the guidewire 16 to penetrate (e.g., cross-through) the lesion. For example, the distal end 16B of the guidewire 16 may be diverted away from the lesion when the distal end 16B contacts the lesion, which may cause the guidewire 16 to jump subintimally into a vessel wall or perforate a vessel wall completely.

The balloon 28 may be formed from any suitable material, such as, but not limited to, polyethylene, polyethylene terephthalate (PET), nylon, a polyether block amide, polytetrafluorethylene (PTFE), polyurethane, polyester, silicone, polyvinyl chloride, polypropylene, polyurethanes, polyamides, latex, natural rubber, synthetic rubber, or the like. In some examples, the balloon 28 may be made of an expandable material (e.g., made of a stretchable material that expands under pressure).

In some examples, the balloon 28 can have structural features (e.g., a roughened surface) or a friction-increasing coating configured to increase the static friction between the balloon 28 and the guidewire 16. This may help the balloon 28, when in an expanded state, grip the guidewire 16 and help secure the catheter 10 and the guidewire 16, e.g., by fixing the relative longitudinal position of the catheter 10 and the guidewire 16. In other examples, however, the balloon 28 is configured to enable the guidewire 16 to longitudinally slide relative to the catheter, even when the balloon 28 is in an expanded configuration. In these examples, the balloon 28 may still provide structural support the balloon 28 and may help keep the guidewire 16 relatively centered in the inner lumen 26, which may help guide the guidewire 16 through a more central portion of a lesion and minimize the risk of the guidewire 16 inadvertently extending through a blood vessel wall.

In some examples, the balloon 28 may be formed separately from the elongated body 12 and connected to the elongated body 12 between the inner wall 20 and the outer wall 21 using any suitable technique. For example, the proximal and the distal ends of the balloon 28 may be bonded (e.g., via adhesive), crimped, swaged, welded, or otherwise secured to the inner and outer walls 20, 21 of the elongated body 12. In other examples, the balloon 28 may be integrally formed with the elongated body 12.

The hub 14 is positioned at the proximal end of catheter 10 and defines an opening through which the inner lumen 26 of the elongated body 12 may be accessed and, in some examples, closed. For example, the hub 14 may include a luer connector for connecting to another device, a hemostasis valve, or another mechanism or combination of mechanisms. In some examples, the catheter 10 includes a strain relief member 11, which may be a part of the hub 14 or may be separate from the hub 14. In other examples, the proximal end of the catheter 10 can include another structure in addition to, or instead of, the hub 14.

The hub 14 may include one or more extension members 32A and 32B (collectively "the extension members 32") in fluid communication with one or more inflation lumens of the elongated body 12, the inflation lumens being in fluid communication with the balloon 28. For example, each of the extension members 32A, 32B may be in fluid communication with a respective inflation lumen or in fluid communication with the same inflation lumen. Thus, the extension members 32 can be used to deliver inflation fluid (e.g., saline) to one or more balloons 28.

Figure 2A:
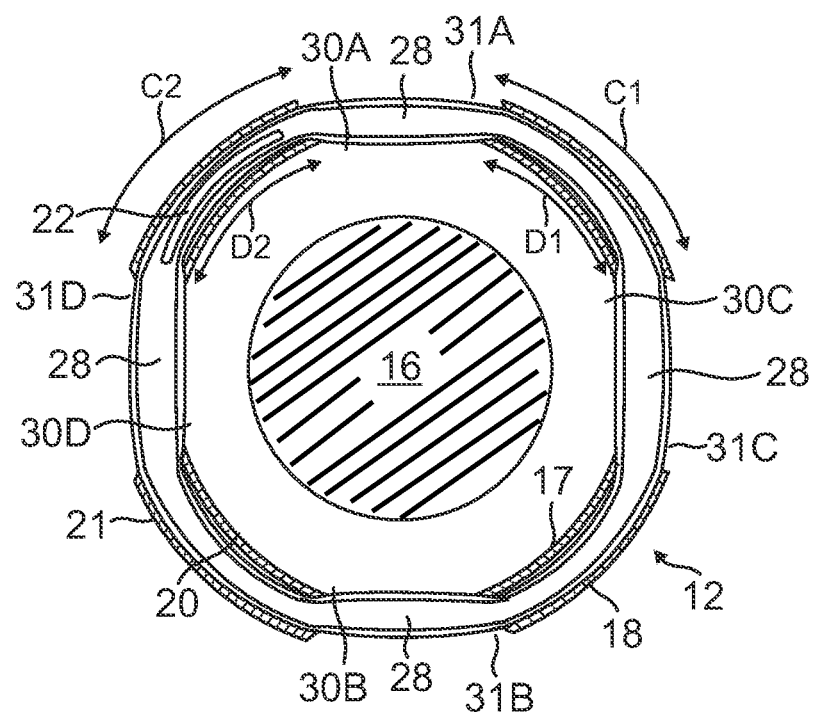
FIG. 2A is a schematic cross-sectional view of the catheter of FIG. 1, the cross-section being taken along line 2A-2A in FIG. 1, and illustrates the one or more balloons in a deflated configuration and a guidewire positioned in an inner lumen of the elongated body.

FIG. 2A is a schematic cross-sectional view of the catheter 10 of FIG. 1, the cross-section being taken along line 2A-2A in FIG. 1, and illustrates the balloon 28 in a deflated (e.g., collapsed or uninflated) configuration and the guidewire 16 positioned in the inner lumen 26 of the elongated body 12. FIG. 2B is a schematic cross-sectional view of the catheter 10 of FIG. 1, the cross-section being taken along line 2A-2A in FIG. 1, and illustrates the balloon 28 in an expanded configuration and engaged with the guidewire 16. In some examples, the expanded configuration is a fully expanded configuration, which is the configuration of the balloon 28 at a predetermined maximum inflation pressure.

In the deflated configuration (shown in FIG. 2A), an outer surface of the balloon 28 is relatively close to the inner and outer walls 20, 21 of the elongated body 12. As shown in FIG. 2A, in some examples, when the balloon 28 is in a deflated configuration, e.g., when no inflation fluid is within the balloon 28, the balloon 28 is completely contained between the inner and outer walls 20, 21. For example, no part of the balloon 28 protrudes past an outermost surface 18 of the outer wall 21 or an innermost surface 17 of the inner wall 20. In other examples, when the balloon 28 is in the deflated configuration, the balloon 28 at least partially protrudes past the outermost surface 18 of outer wall 21 and/or an innermost surface 17 of the inner wall 20.

Figure 2B:
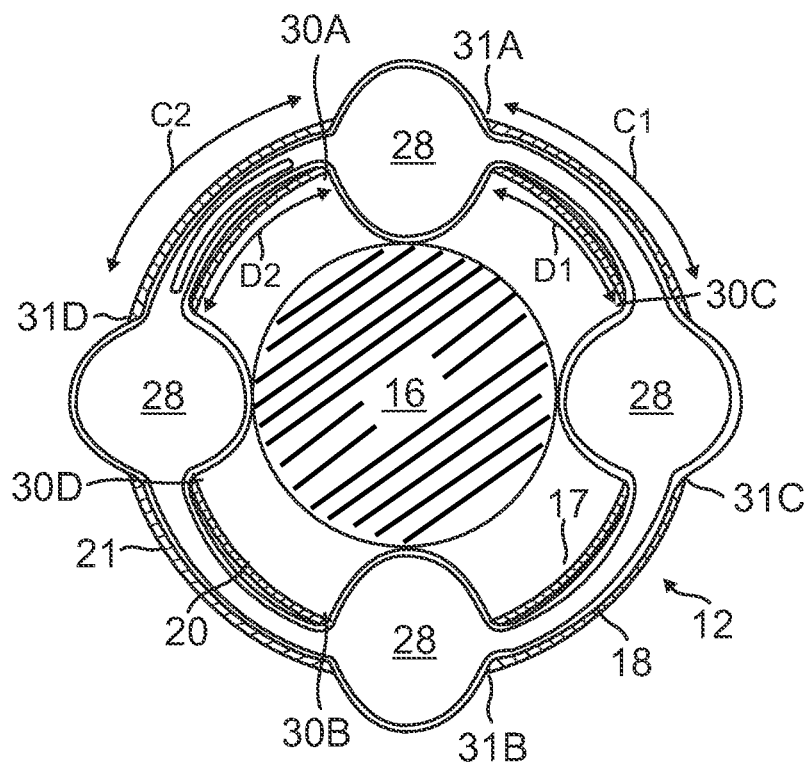
FIG. 2B is a schematic cross-sectional view of the catheter of FIG. 1, the cross-section being taken along line 2A-2A in FIG. 1, and illustrates the one or more balloons in an expanded configuration and engaged with the guidewire positioned in the inner lumen of the elongated body.

As shown in FIG. 2B, in the expanded configuration, the balloon 28 is expanded radially outward through outer wall openings 31A-31D and expanded radially inward through inner wall openings 30A-30D, such that at least some portions of the outer surface of the balloon 28 are expanded away from the outer wall 21 and at least some portion of the outer surface of the balloon 28 are engaged with the guidewire 16. Thus, in the deflated configuration, the balloon 28 has a relatively low profile configuration, and in the expanded configuration, the balloon 28 has a higher profile configuration compared to the deflated configuration. In some examples, in the expanded configuration, the balloon 28 extends a distance of about 0.5 mm to about 5 mm from the outermost surface 18 of the outer wall 21 of when fully expanded.

Although four inner wall openings 30A-30D and four outer wall openings 31A-31D are shown in the example of FIGS. 2A and 2B, in other examples, the inner wall 20 can define any suitable number of inner wall openings 30 and the outer wall 21 can define any suitable number of inner wall openings 30.

The outer wall openings 31 may each have any suitable spacing relative to another. The spacing can include, for example, a circumferential spacing in a direction along the outer wall 21 of the elongated body 12. The circumferential spacing can also be referred to as a tangential spacing in the case of the elongated body 12 having a non-circular cross-section. In some examples, some or all of the outer wall openings 31 are evenly spaced about the outer wall 21 of the elongated body 12. In the example shown in FIG. 2A, a circumferential distance C1 between the outer wall openings 31A and 31C may be the same distance as a circumferential distance C2 between the outer wall openings 31A and 31D (e.g., separated by a distance of about 0.02 mm to about 5 mm). In other examples, some or all of the outer wall openings 31 are unevenly spaced about the outer wall 21 of the elongated body 12. For example, the circumferential distance C1 between the outer wall openings 31A and 31C may be greater than the circumferential distance C2 between the outer wall openings 31A and 31D.

The inner wall openings 30 may each have any suitable spacing relative to another. In some examples, some or all of the inner wall openings 30 are evenly circumferentially spaced along the inner wall 20. In the example shown in FIG. 2A, a circumferential distance D1 between the inner wall openings 30A and 30C may be the same distance as a circumferential distance D2 between the inner wall openings 30A and 30D (e.g., separated by a distance of about 1 mm). In other examples, some or all of the inner wall openings 30 are unevenly spaced about the inner wall 20. For example, the circumferential distance D1 between the inner wall openings 30A and 30C may be greater than the circumferential distance D2 between the inner wall openings 30A and 30D. The circumferential distances between wall openings can be measured, for example, from one side of a wall opening to another side, e.g., the closest parts of adjacent wall openings.

Figure 3A:
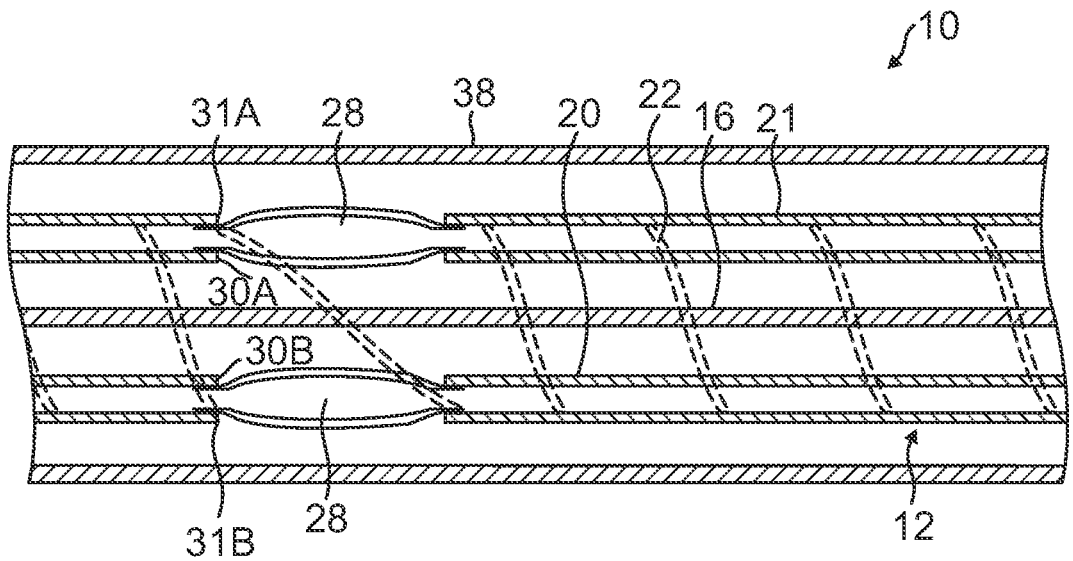
FIG. 3A is a schematic cross-sectional view of the catheter of FIG. 1 in vasculature of a patient, where the cross-section is taken along a central longitudinal axis of an elongated body of the catheter, and illustrates a balloon in a deflated configuration and a guidewire in an inner lumen of the elongated body.
Figure 3B:
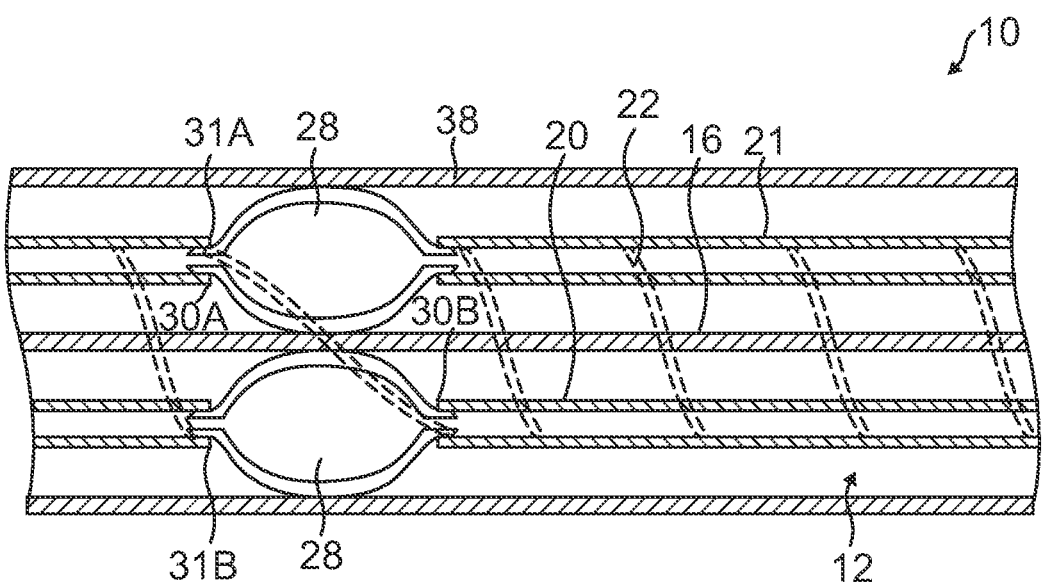
FIG. 3B is a schematic cross-sectional view similar to that shown in FIG. 3A, and illustrates the balloon in an expanded configuration and engaged with the guidewire in the lumen of the elongated body.

FIG. 3A is a schematic cross-sectional view of an example of the catheter 10 of FIG. 1 in a blood vessel 38 of a patient, where the cross-section is taken along the central longitudinal axis A of the elongated body 12 of the catheter 10, and illustrates the balloon 28 in the deflated configuration and the guidewire 16 positioned in the inner lumen 26 of the catheter 10. FIG. 3B illustrates the same view of the blood vessel and the catheter 10, but illustrates the balloon 28 in an expanded configuration and engaged with the guidewire 16.

In the deflated configuration of the balloon 28, the elongated body 12 is in a relatively low profile configuration to better configure the elongated body 12 for navigation through the blood vessel 38 to a target site within a patient. In addition, in the deflated configuration of the balloon 28, the balloon 28 does not interfere with the ability of the guidewire 16 to freely slide within the inner lumen 26. For example, in some examples, when the balloon is in the deflated configuration, the balloon 28 is configured to not contact the guidewire 16 when the guidewire 16 is centered along the central longitudinal axis A of the elongated body 12.

In the example illustrated in FIGS. 3A and 3B, the catheter 10 includes a structural support member 22 positioned between the inner and outer walls 20, 21, where the structural support member 22 includes a coil defining a plurality of turns (e.g., in the shape of a helix). The structural support member 22 may be formed from any suitable material, such as a metal (e.g., a nickel titanium alloy and/or stainless steel), a polymer, or combinations thereof. As an example, the structural support member 22 may be formed from a wire that is arranged to define the coil.

The structural support member 22 defines a gap through which the balloon 28 can expand when expanding through the inner wall openings 30 into the inner lumen 26 and/or when expending through the outer wall openings 31 and away from the outer surface 34 of the elongated body 12. For example, in the example shown in FIGS. 3A and 3B, the gap is defined between turns of the coil, and the balloon 28 can be positioned and configured to expand through the turns of the coil to expand into the inner lumen 26 of the catheter 10 and/or expand through turns of the coil to expand radially from the outer surface 34.

In some examples, the structural support member 22 is a coil having a proximal coil portion having a first pitch, a distal coil portion having a second pitch, and an intermediate coil portion positioned between the proximal and distal coil portions. The intermediate coil portion has a third pitch that is greater than the first pitch and/or the second pitch to define a relatively large gap through which the balloon 28 can expand. The larger the coil pitch, the greater the distance between adjacent winds of the coil. In some examples, the third pitch of the intermediate coil portion is greater than both the first and second pitches of the proximal and distal coil portions, respectively. In some examples, the first and second pitches of the proximal and distal coil portions are substantially equal (e.g., nearly equal to the extent permitted by manufacturing tolerances).

As shown in FIG. 3B, when inflated, the balloon 28 is configured to expand radially outward through the turns of the coil 22 and through the outer wall openings 31A-31D to engage with the wall of the blood vessel 38 to anchor the elongated body 12 in the blood vessel 38. At the same time, the balloon 28 is configured to expand radially inward through the turns of the coil and through the inner wall openings 30A-30B to engage with the guidewire 16 to provide structural support to the guidewire 16. For example, the balloon 28 can directly contact the guidewire 16, e.g., rather than indirectly contacting the guidewire 16 through another layer of the elongated body 12.

Figure 4A:
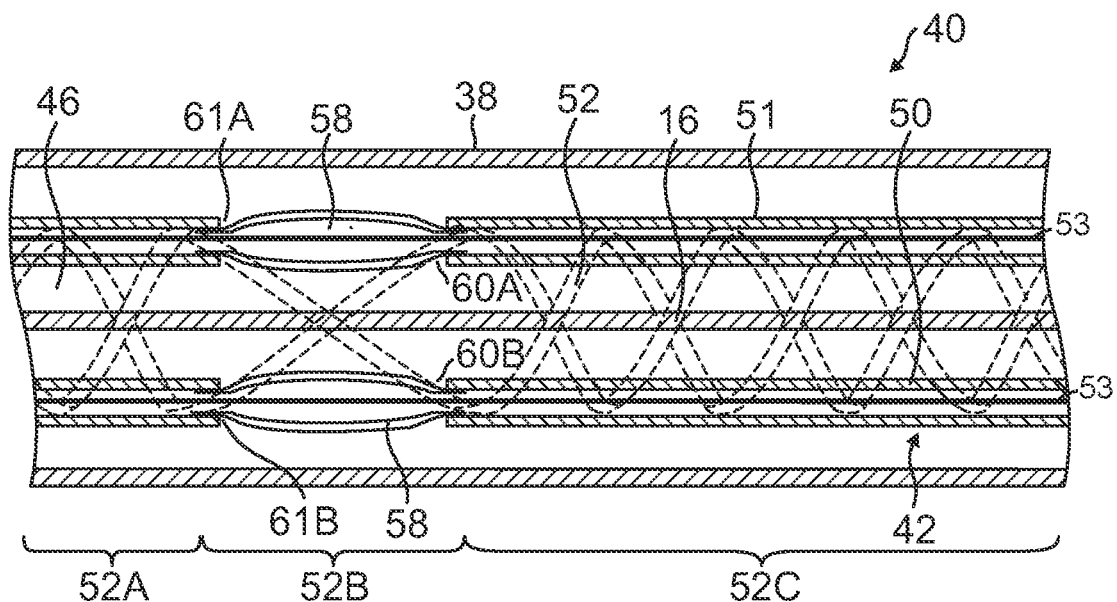
FIG. 4A is a schematic cross-sectional view of another example catheter, where the cross-section is taken along a central longitudinal axis of an elongated body of the catheter, and illustrates an example structural support member between inner and outer walls of the elongated body.
Figure 4B:
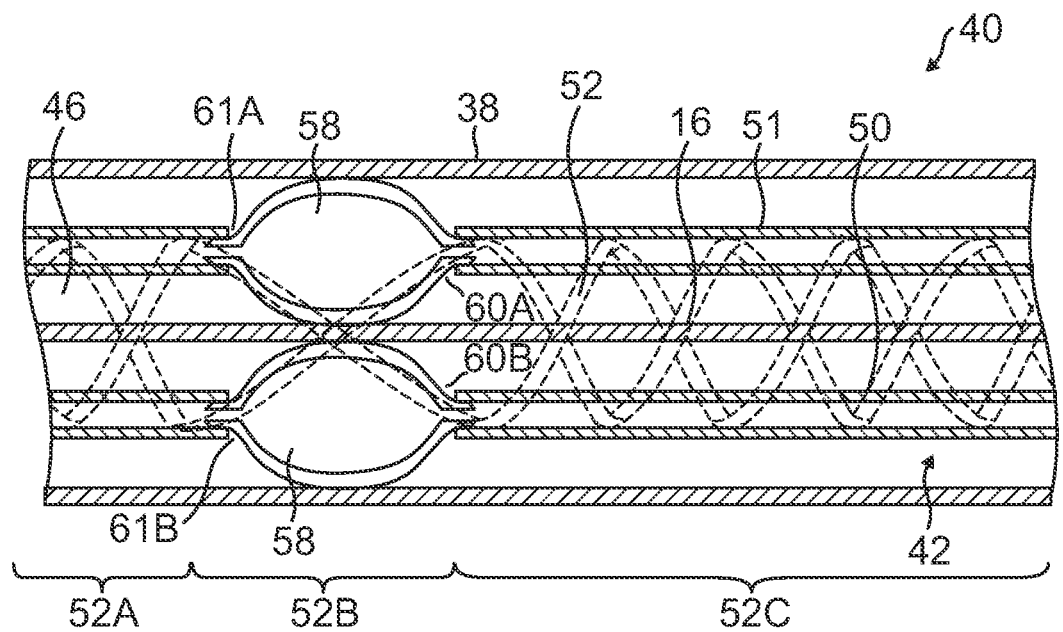
FIG. 4B is a schematic cross-sectional view of the catheter of FIG. 4A, where the cross-section is taken along the central longitudinal axis of the elongated body, and illustrates the balloon in an expanded configuration.

In other examples, the structural support member 22 of the elongated body 12 can include another structure in addition or instead of a coil, such as a braid. FIGS. 4A and 4B are schematic cross-sectional views of another example catheter 40, which is similar to the catheter 10 but includes a braid 52 instead of a coil 22. In other examples, a catheter can include both a braid 52 and a coil 22. The catheter 40 shown in FIGS. 4A and 4B includes an elongated body 42, a balloon 58, and a structural support member including a braid 52. The cross-sections are taken along a central longitudinal axis of an elongated body 42 of the catheter 40. FIG. 4A illustrates the balloon 58 in a deflated configuration and FIG. 4B illustrates the balloon 58 in an expanded configuration. The catheter 40 is shown to be positioned within a blood vessel 38. In the example illustrated in FIG. 4A, the elongated body 42 includes an inner wall 50, an outer wall 51, and the structural support member 52 positioned between the inner and outer walls 50, 51. The catheter 40, the elongated body 42, the inner and outer walls 50, 51, and the balloon 58, and are similar to the catheter, 10, the elongated body 12, the inner and outer walls 20, 21, and the balloon 28, and catheter 10 of FIGS. 1-3B, except for the differences described herein.

The braid 52 includes a structure defined by braided wires (e.g., wire filaments), such as metal wires (e.g., a nickel titanium alloy and/or stainless steel). The braids can be formed by, for example, a plurality of wires braided in any suitable pattern, such as, but not limited to, a one-under-two pattern, an over-two pattern, a two-under-two, over-two pattern, or the like. The braid 52 defines a plurality of pics. The point at which the material (e.g., filaments) forming the braid 52 cross-over one another is referred to herein as a "pic" and braid density can be measured in "pics per inch" ("PPI"). The braid density may be adjusted by increasing or decreasing the number of pics along the length of the braid 52.

The braid 52 includes a proximal braid portion 52A, an intermediate braid portion 52B, and a distal braid portion 52C, where the intermediate braid portion 52B is positioned between the proximal and distal braid portions 52A, 52C. In some examples, the braid 52 has a unibody construction braid, such that the proximal, intermediate, and distal braid portions 52A-52C are part of a seamless braid. The unibody construction braid 52 may help the elongated body 42 to better distribute forces in a longitudinal direction and rotational direction compared to an elongated body including multiple braid portions that are mechanically connected to each other.

The inner and outer walls 50, 51 define inner wall openings 60A and 60B (collectively "inner wall openings 60") and outer wall openings 61A and 61B (collectively "outer wall openings 61"), through which the balloon 58 is configured to expand. The intermediate braid portion 52B is aligned with the inner wall openings 60 and the outer wall openings 61, such that the balloon 58 is configured to expand through the braid 52 along the intermediate braid portion 52B. To help accommodate this, the intermediate braid portion 52B may have a braid density less than a braid density of the proximal braid portion 52A and/or a braid density of the distal braid portion 52C. For example, the intermediate braid portion 52B has a braid density of 2 PPI to about 50 PPI, while the proximal braid portion 52A and/or the distal braid portion 52C has a braid density of 100 PPI to 250 PPI. In some examples, the proximal braid portion 52A and the distal braid portion 52C have the same braid densities. In other examples, however, the proximal braid portion 52A and the distal braid portion 52C have different braid densities.

In some examples, the length of the intermediate braid portion 52B may be based on the length of the balloon 58. For example, the intermediate braid portion 2 may be any suitable length for the balloon 58 to expand through, such as, but not limited to, about 0.2 cm to about 5 cm, such as about 0.5 cm, about 2 cm, or about 3 cm. In some examples, for a given wire size, the braid density of the braid 52 is correlated with the stiffness of the braid 52. A braid portion with a relatively low braid density has fewer pics (fewer cross-over points) compared to a braid portion with a relatively higher braid density, which may cause the braid portion with the relatively low density to have a higher stiffness relative to the braid portion with the relatively high braid density.

In some examples, the intermediate braid portion 52B with a relatively lower braid density may be aligned with the inner wall and outer wall openings 60, 61. The inner wall and outer wall openings 60, 61 may define points of relative weakness along the elongated body 42 and, as a result, the elongated body 42 may be more likely to kink along the regions having the inner wall and outer wall openings 60, 61. Aligning the intermediate braid portion 52B having a relatively lower braid density and corresponding higher stiffness with the inner wall and outer wall openings 60, 61 can help compensate for this weakness along the elongated body 42, and therefore help minimize the possibility of kinking at the regions of the elongated body 42 having the inner wall and outer wall openings 60, 61. The intermediate braid portion 52B with a relatively low braid density and corresponding higher stiffness may also maintain pushability of the elongated body 42 and torque transmission from a proximal end of the catheter 40 to a distal end of the catheter 40 by compensating for any weakness to the elongated body 42 resulting from the presence of the inner wall and outer wall openings 60, 61.

As shown in FIG. 4B, the balloon 58 is configured to expand through the pics of the intermediate portion 52B of the braid 52. The balloon 58 is configured to expand radially outward through the pics of the braid 52 and through the outer wall openings 61 to engage with vessel walls of the blood vessel 38. At the same time, the balloon 58 is configured to expand radially inward through the pics of the braid 52 and through the inner wall openings 60 to engage with the guidewire 16 positioned in an inner lumen 46 of the elongated body 42. Thus, when inflated, the balloon 58 may engage the guidewire 16 and walls of the vessel 38 at the same time to provide support to the guidewire 16 while anchoring the catheter 40 in the vessel 38. Without the balloon 58, the guidewire 16 may be more prone to buckling or jumping when the distal end of the guidewire 16 contacts a lesion within the vessel 38 and the elongated body 42 may tend to move, e.g., out of the artery, which may cause poor penetration of the lesion. Thus, the catheter 40 described herein may provide support to the guidewire 16 to avoid or reduce guidewire buckling or guidewire jumping and help free up the hands of clinicians during a medical procedure by inflating the balloon 58 that is part of the catheter 40.

In some examples, in addition to or instead of a structural support member 52 such as a coil or a braid, the catheter 40 or any of the other catheters described herein include one or more axial wires 53 that extend along at least part of a length of the catheter (measured from the proximal end to the distal end of the catheter). The axial wires 53 are configured to add structural support, e.g., column strength, to the elongated body 42 as it is navigated through tortuous anatomy. The axial wires 53 may be substantially straight (e.g., straight or nearly straight to the extent permitted by manufacturing tolerances) and may extend along a longitudinal axis of the elongated body 42. The axial wires 53 may be positioned between the inner wall 50 and the outer wall 51. In examples in which the catheter 42 also includes the braid 52 (or another structural support member), the axial wires 53 may be positioned between the outer wall 51 and the braid 52 and/or between the inner wall 50 and the braid 52. The axial wires 53 help distribute the flexibility provided by the braid 52 (or other structural support member) along a length of the braid 52. For example, eliminating voids between pics of the structural support member 52, the axial wires may transfer the flexing motion from the structural support member 52 along a length of the catheter 40.

Figure 5A:
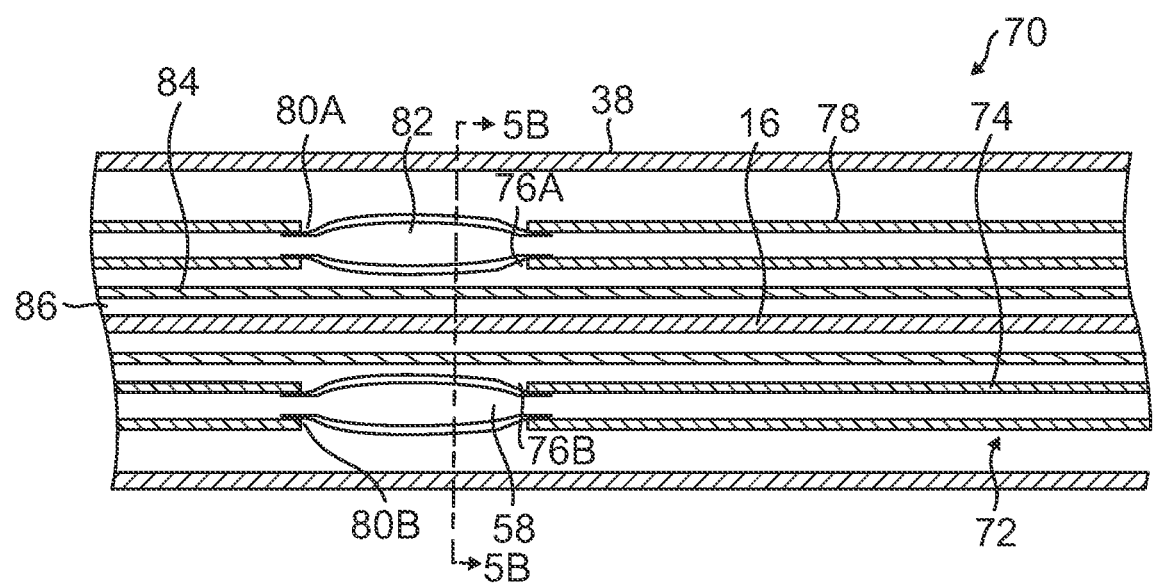
FIG. 5A is a schematic cross-sectional view of an example catheter including an inner liner in addition to inner and outer walls, where the cross-section is taken along a central longitudinal axis of an elongated body of the catheter.
Figure 5B:
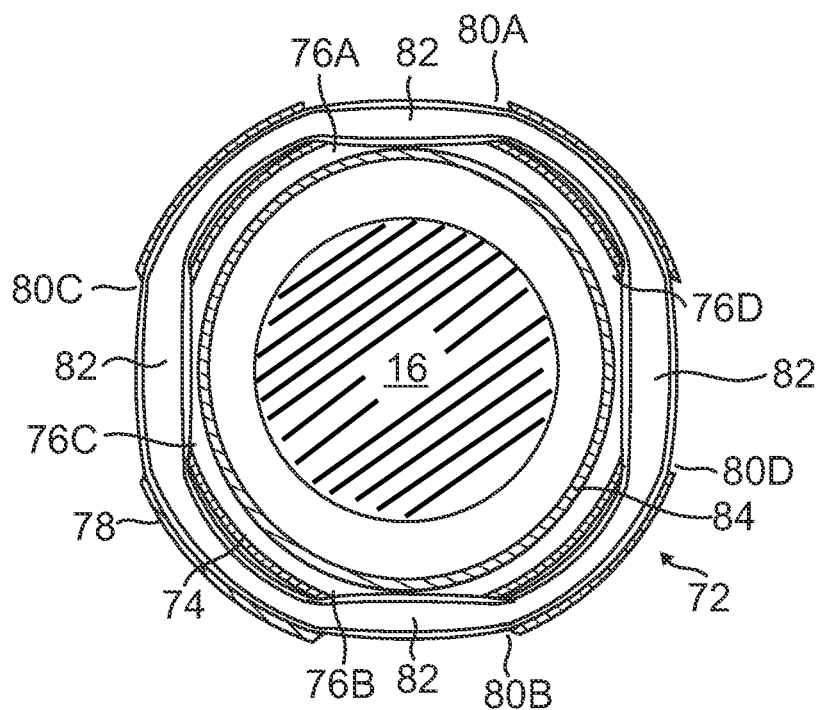
FIG. 5B is a schematic cross-sectional view of the catheter of FIG. 5A, where the cross-section being taken along line 5B-5B in FIG. 5A, and illustrates the balloon in a deflated configuration and an inner liner between the inner and outer walls of the elongated body.
Figure 5C:
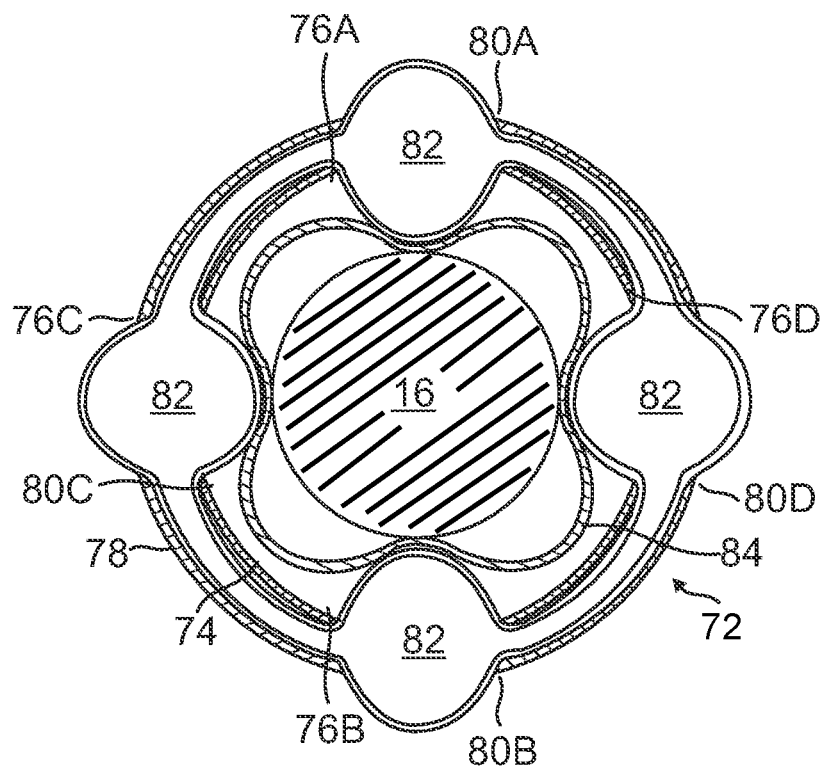
FIG. 5C is a schematic cross-sectional view of the catheter of FIG. 5A, the cross-section being taken along line 5B-5B in FIG. 5A, and illustrates the balloon in an expanded configuration and engaged with the inner liner, where the inner liner is engaged with the guidewire positioned in the inner lumen of the elongated body.

In some example catheters described herein, such as the catheters 10, 40 described with reference to FIGS. 2A-4B, the catheters are configured such that the respective balloons 28, 58 are configured to directly contact the guidewire 16 positioned within the respective inner lumen 26, 46. In other examples of catheters described herein, the catheter includes an inner liner positioned between the balloon and the guidewire 16, such that when the balloon is in an inflated configuration, the balloon indirectly contacts the guidewire 16. FIGS. 5A-5C illustrate an example catheter 70 that includes an elongated body 72 including an inner wall 74 defining a plurality of inner wall openings 76A-76D, an outer wall 78 defining a plurality of outer wall openings 80A-80D, a balloon 82, and an inner liner 84 radially inward of the inner wall 74. FIGS. 5B and 5C are a schematic cross-sectional view of the catheter of FIG. 5A, where the cross-section is taken along line 5B-5B in FIG. 5A and orthogonal to a central longitudinal axis of the elongated body 72. The balloon 82 is in a deflated configuration in FIG. 5B, and an expanded (inflated) configuration in FIG. 5C.

The inner liner 84 defines an inner lumen 86 of the elongated body 72. At least the inner surface of the inner liner 84 may be lubricious in some examples in order to facilitate the introduction and passage of a medical device, such as the guidewire 16. For example, the material from which the entire inner liner 84 is formed may be lubricious, or the inner liner 84 may be formed from two or more materials, where the material that defines the inner surface of the inner liner 84 may be more lubricious than the material that interfaces with the inner wall 74. In addition to, or instead of, being formed from a lubricious material, in some examples, the inner surface of the inner liner 84 is coated with a lubricious coating.

Example materials from which the inner liner 84 may be formed include, but are not limited to, polytetrafluoroethylene (PTFE), fluoropolymer, perfluoroalkoxy alkane (PFA), fluorinated ethylene propylene (FEP), or any combination thereof. For example, the inner liner M may be formed from a non-etched PTFE, e.g., may consist essentially of a non-etched PTFE.

In some examples, at least part of the inner liner 84 may be connected to the inner wall 74 of the elongated body 72. For example, the inner wall 74 and the inner liner 84 may be adhered or bonded together along their respective lengths, except where the inner wall 74 defines the inner wall openings 76A-76D. as another example, the inner wall 74 and the inner liner 84 may be adhered or bonded together along only part of their respective lengths.

As shown in FIG. 5B, when the balloon 82 is in a deflated configuration, e.g., when no inflation fluid is within the balloon 82, the balloon 82 may be contained between the inner and outer walls 74, 78 and may not extend through the inner wall openings 76A-76D or the outer wall openings 80A-80D. As shown in FIG. 5C, in the expanded configuration, the balloon 82 extends radially outward through outer wall openings 80A-80D and expanded radially inward through the inner wall openings 76A-76D, such that at least some portions of the outer surface of the balloon 28 are engaged with the inner liner 84 and pushes the inner liner 84 towards the guidewire 84 and into engagement with the guidewire 16. In some examples, to help increase the ability of the balloon 82 to fix a position of the guidewire 16 and the catheter 70, the inner liner 84 can include a surface treatment (e.g., etching) to increase the static friction between the inner liner 84 and the guidewire 16 when the balloon 82 expands through the inner wall openings 76A-76D and brings the inner liner 84 into engagement with the guidewire 16.

Although not shown in FIGS. 5A-5C, in some examples, the catheter 70 includes a structural support member such as the coil 22 (FIGS. 3A and 3B) or the braid 52 (FIGS. 4A and 4B), and the balloon 82 may be configured to expand through gaps defined by the structural support member.

As discussed with reference to FIGS. 5 and 6, instead of a single balloon 28, in some examples, a catheter may include a plurality of balloons. The balloons may be in fluid communication with one or more inflation lumens defined by an elongated body of the catheter and are configured to receive an inflation fluid via the one or more inflation lumen to expand from a respective deflated configuration to a respective expanded configuration. The plurality of balloons may each be deflated via the one or more inflation lumens as well. In some examples, at least two balloons of the plurality of balloons may be fluidically coupled to separate inflation lumens. Instead of or in addition to this configuration, as discussed with reference to FIG. 6, in some examples, at least two balloons of the plurality of balloons may be fluidically coupled to the same inflation lumen.

While FIGS. 1-5C shows catheters having a single balloon, in some examples, more than one balloon may be connected to an elongated body of a catheter between an inner wall and the outer wall of the catheter. FIG. 6 is a schematic cross-sectional view of another example catheter 90 in a blood vessel 38 of a patient, where the cross-section is taken along a central longitudinal axis of an elongated body 92 of the catheter 90. The catheter 90 includes a plurality of balloons, including a balloon 94A and a balloon 94B (collectively, "balloons 94") positioned between an inner wall 91 and an outer wall 93 and configured to extend through openings defined in the inner wall 91 and the outer wall 93. Although not shown in FIG. 6, the catheter 90 can also include an inner liner (e.g., the inner liner 84 shown in FIGS. 4A-5C) radially inward of the inner wall 91. The catheter 90, including the elongated body 92 and the balloons 94, are similar to the catheters 10, 40 except for differences described herein. Thus, the description of the elongated bodies 12, 42 and the balloons 28, 58 are also applicable to the elongated body 92 and balloons 94.

At least two balloons of the plurality of balloons 94 are fluidically coupled to separate inflation lumens, which enables the at least two balloons to be separately inflated via an inflation fluid 96 (e.g., saline) delivered via the respective inflation lumen. For example, in the example shown in FIG. 6, the elongated body 92 defines at least two separate inflation lumens 98A and 98B (collectively "inflation lumens 98"), which may be fluidically coupled to respective the balloons 94A, 94B and to respective extension members 32A, 32B (shown in FIG. 1). The balloon 94A is fluidically coupled to an inflation lumen 98A and not an inflation lumen 98B, and the balloon 94B is fluidically coupled to the inflation lumen 98B, but not the inflation lumen 98A. That is, the inflation lumen 98B is fluidically isolated from and not fluidically coupled to balloon 94A, and the inflation lumen 98A is fluidically isolated from and not fluidically coupled to balloon 94B. Thus, the catheter 90 is configured such that a clinician can inflate a subset of the plurality of balloons 94 (e.g., one balloon or more than one balloon but less than all the balloons 94) selectively during a medical procedure. For example, in FIG. 6, the balloon 94A is shown to be in a deflated configuration and the balloon 94B is shown to be in an inflated configuration.

Configuring at least one balloon 94 to be fluidically coupled to a separate inflation lumen from another balloon may enable the clinician to tailor the anchoring mechanism of catheter 90 to a target anchor site by selecting the balloons 94 to expand based on a length of a blood vessel 38 in which an elongated body 92 of the catheter 90 will be anchored. In addition, an ability to selective inflate a subset of the balloons 94 may enable the clinician to use the balloons 94 to, for example, facilitate navigation of the elongated body 92 to the target site within a patient. For example, a clinician may selectively inflate the balloon 94B to its expanded configuration while leaving the balloon 94A fully deflated or only partially inflated to better center the elongated body 92 in the blood vessel 38, e.g., when navigating the elongated body 92 around a curve, or to push the guidewire 16 to one side of the lumen 95, as shown in FIG. 6. At the same time, when inflated, the balloon 94B may apply a force directed radially inwards, to engage with and re-center the guidewire 16 in the blood vessel 38.

In other examples, at least two balloons of the balloons 94 are fluidically coupled to a common inflation lumen. For example, the elongated body 92 may define only one inflation lumen that is fluidically coupled to all of the balloons 94 and is used to deliver the inflation fluid 96 all of the balloons 94. As another example, the elongated body 92 may define multiple inflation lumens, but at least one of the inflation lumens is fluidically coupled to at least two balloons 94. An example of such a configuration is shown in FIG. 7, which illustrates an example catheter 100 including an elongated body 102 that is similar to the catheter 90 and the elongated body 92 of FIG. 6, except that the inflation lumen 98A is in fluid communication with at least two balloons 94A, 94C and the inflation lumen 98B is in fluid communication with at least two balloons 94B, 94D. In some examples, the inflation lumens 98A, 98B are fluidically coupled, e.g., are formed by annular-ring shaped inflation lumen that is defined by the space between the inner wall 91 and the outer wall 93 of the elongated body 92.

Figure 6:
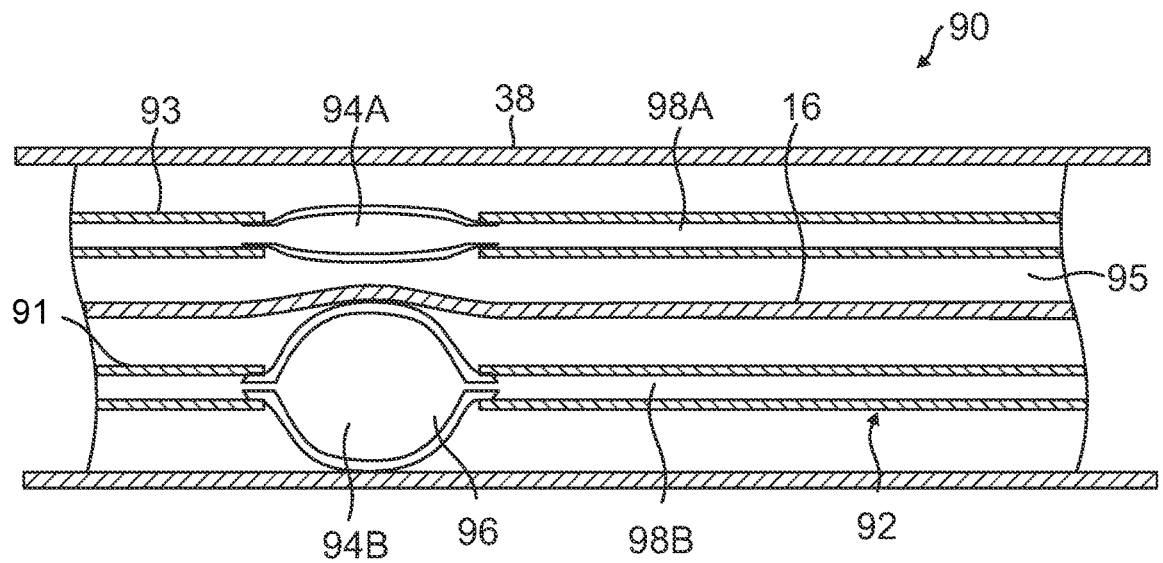
FIG. 6 is a schematic cross-sectional view of another example catheter in vasculature of a patient, where the cross-section is taken along a central longitudinal axis of an elongated body of the catheter, and illustrates a balloon in a deflated configuration and another balloon in an expanded configuration.
Figure 7:
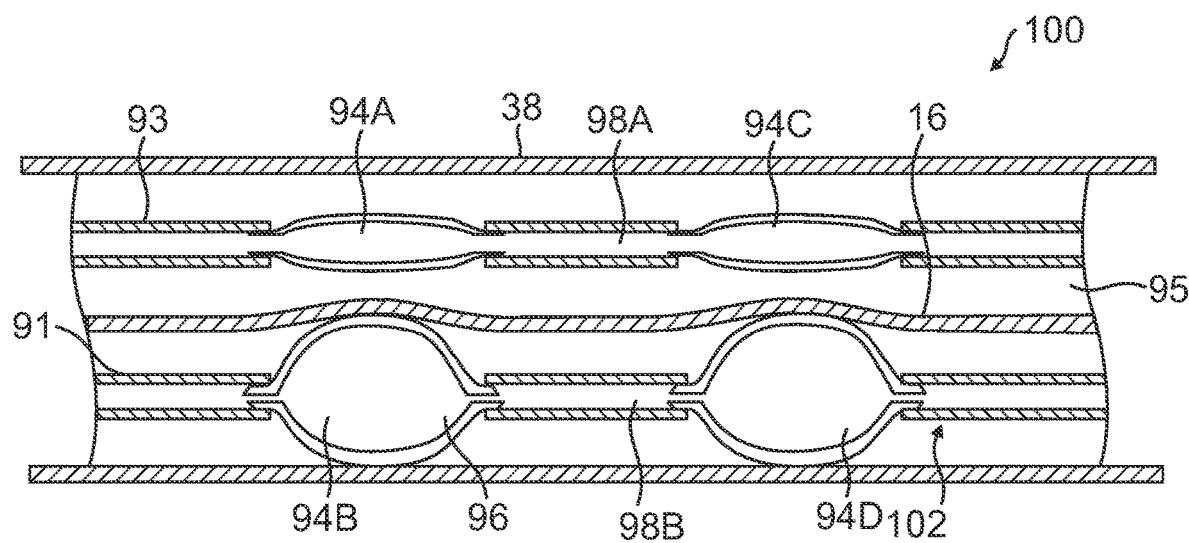
FIG. 7 is a schematic cross-sectional view of another example catheter in vasculature of a patient, where the cross-section is taken along a central longitudinal axis of an elongated body of the catheter, and illustrates a plurality of balloons, where a subset of the plurality of balloons is in a deflated configuration and another subset of the plurality of balloons is in an expanded configuration.

In the example of FIG. 6, FIG. 7, or any other example in which a catheter includes multiple balloons, the balloons may be configured to expand to the same diameter or different diameters. Configuring the balloons, such as balloon 94B, 94D to expand to different diameters may provide a clinician with different options to tailor a given catheter for use with different blood vessel sizes.

The balloon 28 may be inflated to any suitable pressure via an inflation fluid (e.g., saline) delivered to the balloon 28 via an inflation lumen defined by the elongated body 12 (e.g., between the inner and outer walls 20, 21).

Figure 8:
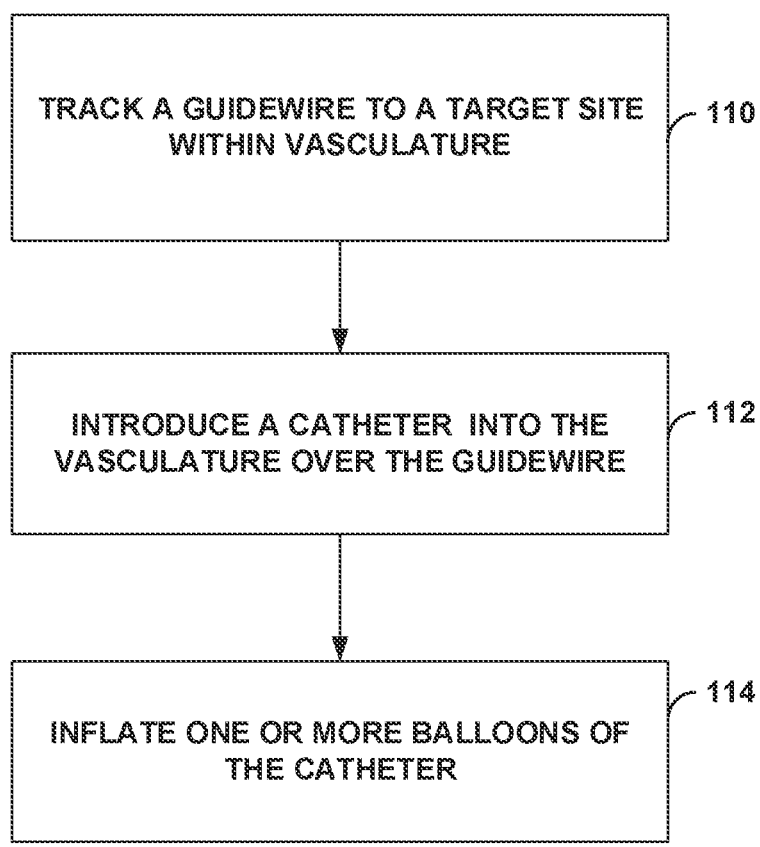
FIG. 8 is a flow diagram of an example method of using a catheter including at least one balloon between an inner wall and an outer wall of the catheter.

FIG. 8 is a flow diagram of an example method of using a catheter including at least one balloon between an inner wall and an outer wall of the catheter. FIG. 8 is primarily described below with reference to the catheter 10 of FIGS. 1-3B. However, in other examples, the example technique may be used with other catheters described herein.

In the method shown in FIG. 8, a clinician may track a guidewire 16 from a suitable access point (e.g., a femoral artery or a radial artery) to a target site within the vasculature of a patient (110) and introduce the catheter 10 into the vasculature over the already-positioned guidewire 16 (112). In some examples, the clinician may track the guidewire 16 and the catheter 10 to the target site through a guide catheter.

The clinician may inflate the one or more balloons 28 of the catheter 10 to an expanded configuration (114). For example, the clinician may deliver the inflation fluid via separate inflation lumens (e.g., 98A, 98B) to inflate balloons (e.g., balloons 94A and 94B) separately or via a single inflation (e.g., inflation lumen 98) to at least two balloons (e.g., balloons 94B, 98D) to expand the balloons to an expanded configuration (FIGS. 6 and 7). As described above, when the one or more balloons 28 are in an expanded configuration (e.g., as shown in FIG. 2B), the one or more balloons 28 are configured to expand radially outward through one or more outer wall openings 31 to anchor the elongated body 12 of the catheter 10 within the vessel 38. At the same time, the one or more balloons 28 are configured to expand radially inward through one or more inner wall openings 30 to provide structural support to the guidewire 16 positioned in the inner lumen 26 of the elongated body 12 to prevent and reduce guidewire buckling or guidewire jumping when the distal end of the guidewire 16 contacts a relatively rigid material, e.g., a lesion or other occlusion within the vessel 38 of a patient, which provides better therapeutic outcomes.

Various examples have been described. These and other examples are within the scope of the following claims.

What is claimed is:

1. A catheter comprising:
    an elongated body defining a lumen, the elongated body comprising:
        an inner wall defining an inner wall opening; and
        an outer wall defining an outer wall opening; and
    a balloon connected to the elongated body between the inner wall and the outer wall, wherein the balloon is configured to expand through the inner wall opening into the lumen of the elongated body, and wherein the balloon is configured to expand through the outer wall opening to engage with a wall of a blood vessel.

2. The catheter of claim 1, wherein the balloon is configured to expand through the inner wall opening into the lumen to contact a guidewire positioned within the lumen.

3. The catheter of claim 1, further comprising a structural support member positioned between the inner wall and the outer wall, the structural support member defining a gap, wherein the balloon is configured to expand through the gap.

4. The catheter of claim 3, wherein the structural support member comprises a coil, and wherein the gap is defined between turns of the coil.

5. The catheter of claim 4, wherein the coil comprises a proximal coil portion having a first pitch, a distal coil portion having a second pitch, and an intermediate coil portion between the proximal and distal coil portions, the intermediate coil portion having a third pitch greater than at least one of the first pitch or the second pitch.

6. The catheter of claim 3, wherein the structural support member comprises a braid, and wherein the gap is defined by pics of the braid.

7. The catheter of claim 6, wherein the braid comprises a proximal braid portion having a first braid density, a distal braid portion having a second braid density, and an intermediate braid portion between the proximal and distal braid portions, the intermediate braid portion having a third braid density less than at least one of the first braid density or the second braid density.

8. The catheter of claim 7, wherein the proximal braid portion, the distal braid portion, and the intermediate braid portion have a unibody construction.

9. The catheter of claim 7, wherein the inner wall opening and the outer wall opening are aligned with the intermediate braid portion along a longitudinal axis of the elongated body.

10. The catheter of claim 1, wherein the inner wall defines a plurality of inner wall openings, the plurality of inner wall openings including the inner wall opening, and wherein the outer wall defines a plurality of outer wall openings, the plurality of outer wall openings including the outer wall opening, and wherein the balloon is configured to expand through the plurality of inner wall openings into the lumen and through the plurality of outer wall openings.

11. The catheter of claim 1, wherein the catheter comprises a plurality of balloons including the balloon, wherein the inner wall defines a plurality of inner wall openings, the plurality of inner wall openings including the inner wall opening, and wherein the outer wall defines a plurality of outer wall openings, the plurality of outer wall openings including the outer wall opening, and
    wherein each balloon of the plurality of balloons is configured to expand through a respective inner wall opening of the plurality of inner wall openings and through a respective outer wall opening of the plurality of outer wall openings.

12. The catheter of claim 11, wherein the elongated body defines an inflation lumen, and wherein at least two balloons of the plurality of balloons are fluidically coupled to the inflation lumen.

13. The catheter of claim 11, wherein the elongated body defines a plurality of inflation lumens, and wherein at least two balloons of the plurality of balloons are fluidically coupled to separate inflation lumens of the plurality of inflation lumens.

14. A system comprising:
    the catheter of claim 1; and
    a guidewire within the lumen of the elongated body, wherein the balloon is configured to expand through the inner wall opening into the lumen to directly contact the guidewire and secure the guidewire relative to the catheter.

15. A catheter comprising:
    an elongated body defining a lumen, the elongated body comprising:
        an inner wall defining a plurality of inner wall openings;
        an outer wall defining a plurality of outer wall openings; and
        a structural support member positioned between the inner wall and the outer wall,
    wherein the structural support member defines a gap; and
    a balloon connected to the elongated body between the inner wall and the outer wall, wherein the balloon is configured to expand through the plurality of inner wall openings into the lumen of the elongated body and through the plurality of outer wall openings, and through the gap defined by the structural support member.

16. The catheter of claim 15, wherein the plurality of inner wall openings and the plurality of outer wall openings are aligned with each other.

17. The catheter of claim 15, wherein at least one of the plurality of inner wall openings or the plurality of outer wall openings are distributed around an outer perimeter of the inner wall or the outer wall, respectively.

18. A system comprising:
    the catheter of claim 15; and
    a guidewire positioned within the lumen of the elongated body, wherein the balloon is configured to expand through the plurality of inner wall openings into the lumen to directly contact the guidewire and secure the guidewire relative to the catheter.

19. A method comprising:
    introducing a catheter into vasculature of a patient, the catheter comprising:
        an elongated body defining a lumen, the elongated body comprising:
            an inner wall defining an inner wall opening; and
            an outer wall defining an outer wall opening; and
        a balloon connected to the elongated body between the inner wall and the outer wall; and
    inflating the balloon to expand the balloon through the inner wall opening into the lumen and to expand through the outer wall opening to engage with a wall of a blood vessel.

20. The method of claim 19, wherein introducing the catheter into the vasculature comprises introducing the catheter over a guidewire, and wherein inflating the balloon comprises inflating the balloon to expand the balloon through the inner wall opening and into the lumen to directly contact the guidewire and secure the guidewire relative to the catheter.

21. The method of claim 19, wherein the catheter further comprises a structural support member positioned between the inner wall and the outer wall, the structural support member defining a gap, and wherein inflating the balloon comprises inflating the balloon to expand the balloon through the gap.

22. The method of claim 19, wherein the inner wall defines a plurality of inner wall openings, the plurality of inner wall openings including the inner wall opening, and wherein the outer wall defines a plurality of outer wall openings, the plurality of outer wall openings including the outer wall opening, and wherein inflating the balloon comprises inflating the balloon to expand the balloon through the plurality of inner wall openings into the lumen and through the plurality of outer wall openings.

23. The method of claim 19, wherein the catheter comprises a plurality of balloons including the balloon, wherein the inner wall defines a plurality of inner wall openings, the plurality of inner wall openings including the inner wall opening, and wherein the outer wall defines a plurality of outer wall openings, the plurality of outer wall openings including the outer wall opening, wherein inflating the balloon comprises inflating the plurality of balloons to expand each balloon of the plurality of balloons through a respective inner wall opening of the plurality of inner wall openings and through a respective outer wall opening of the plurality of outer wall openings.

24. The method of claim 23, wherein the elongated body defines an inflation lumen fluidically coupled to at least two balloons of the plurality of balloons, and wherein inflating the plurality of balloons comprises introducing an inflation fluid into the inflation lumen.

25. The method of claim 23, wherein the elongated body defines a plurality of inflation lumens, wherein at least two balloons of the plurality of balloons are fluidically coupled to separate inflation lumens of the plurality of inflation lumens, and wherein inflating the plurality of balloons comprises separately inflating at least two balloons of the plurality of balloons by at least introducing inflation fluid into the respective inflation lumens.

\* \* \* \* \*